(12) United States Patent
Teather et al.

(10) Patent No.: US 6,255,080 B1
(45) Date of Patent: Jul. 3, 2001

(54) BACTERIOCINS PRODUCED BY RUMINAL BACTERIA

(75) Inventors: Ronald M. Teather; Robert J. Forster, both of Lethbridge; Martin Kalmokoff, Ottawa, all of (CA)

(73) Assignee: Her Majesty the Queen in right of Canada, as represented by the Minister of Agriculture and Agri-Food, Ottawa (CA)

( * ) Notice: Subject to any disclaimer, the term of this patent is extended or adjusted under 35 U.S.C. 154(b) by 0 days.

(21) Appl. No.: 08/945,625

(22) PCT Filed: Apr. 26, 1996

(86) PCT No.: PCT/CA96/00269

§ 371 Date: Jan. 5, 1998

§ 102(e) Date: Jan. 5, 1998

(87) PCT Pub. No.: WO96/34014

PCT Pub. Date: Oct. 31, 1996

Related U.S. Application Data

(63) Continuation-in-part of application No. 08/430,957, filed on Apr. 28, 1995, now abandoned.

(51) Int. Cl.[7] .............................. C12P 21/02; C12P 1/00; C07K 1/00; C07K 14/00
(52) U.S. Cl. ...................... 435/71.3; 435/71.1; 435/71.2; 435/41; 435/243; 435/801; 530/350; 530/820; 530/825
(58) Field of Search ..................................... 530/350, 820, 530/825; 435/41, 71.1, 71.2, 71.3, 243, 801

(56) References Cited

PUBLICATIONS

Hespell (Appl Environ Microbiol 54(8)=1917–1922), 1988.*
Hespell (Appl Environ Microbiol 57 (9)=2703–2709), 1991.*
Cotta (Appl Environ Microbiol 52(1)=51–58, 1986.*
Jarvis (J Gen Microbiol 105(2)=287–296), 1978.*
Ware et al. (Curr Microbiol 24(4)=193–197), 1992.*
Sneath et al. (Bergey's Manual of Systematic Bateriology p. 1378–1379), 1986.*
Ha et al (Appl Environ Microbiol 57(7)=2016–2020), 1991.*
Hespell et al (Appl Environ Microbiol 53(12)=2849–2853), 1987.*
Hespell Appl Enviro Microbiol 54 (8) 1917–1922, 1988.*
Hespell Appl Enviro Microbiol 53 (13) 2849–2853, 1987.*
Ha Appl Enviro Microbiol 57 (7)=2016–2020, 1991.*
Jarvis, "Lysis of viable rumen bacteria in bovine rumen fluid" *Appl. Microbiol*, (1968) 16(5):714–723.
Tagg et al., "Bacteriocins of gram–positive bacteria" *Bacteriological Reviews* (1976) 40:722–756.
Iverson et al., "Bacteriocins of *Streptococcus bovis*" *Can. J. Microbiol.* (1976) 22:1040–1047.
Lindgren et al., "Antibacterial activity of lactic acid bacteria" *Swedish J. agric. Res.* (1978) 8:67–73.
Bryant, "Genus IV. Butyrivibrio" *Bergey's Manual of Systemic Bacteriology*, vol. 2, Sneath et al, eds., Williams & Wilkins, 1986, pp. 1376–1379.
Seale, "Bacterial inoculants as silage additives" *J. Appl. Bacteriol. Symposium Suppl.* (1986) pp.9S–26S.
Lindren et al., "Antagonistic activities of lactic acid bacteria in food and feed fermentations" *FEMS Microbiol. Rev.* 87(1990) pp. 149–163.
Meghrous et al., "Screening of Bifidobacterium strains for Bacteriocin production" *Biotechnol. Lett.* (1990) 12(8):575–580.
Toba et al., "Reutericin 6, a new bacteriocin produced by *Lactobacillus reuteri* LA 6" *Lett. in Appl. Microbiol.* (1991) 13:281–286.
Toba et al., "Acidophilucin A, a new heat–labile bacteriocin produced by *Lactobacillus acidophilus* LAPT 1060" *Lett. in Appl. Microbiol*, (1990) 12:106–108.
Piard et al., "Inhibiting factors produced by lactic acid bacteria. 2. Bacteriocins and other antibacterial substances" *Lait* (1992) 72:113–142.
Fitzsimmons et al., "Assessment of *Pediococcus acidilactici* as a potential silage inoculant" *Appl. Env. Microbiol*, (1992) 58(9):3047–3052.
Arihara et al., "Characterization of bacteriocins from *Enterococcus faecium* with activity against *Listeria monocytogenes*" *International J. Food Microbiol*, (1993) 19:123–134.
Nissen–Meyer et al., "Association of the lactococcin A immunity factor with the cell membrane: purification and characterization of the immunity factor" *J. General Microbiol.* (1993) 139:1503–1509.
Bruno et al., "Common mechanistic action of bacteriocins from lactic acid bacteria" *Appl. Env. Microbiol.* (1993) 59(9):3003–3010.

(List continued on next page.)

Primary Examiner—Lynette R. F. Smith
Assistant Examiner—Li Lee
(74) Attorney, Agent, or Firm—Morrison & Foerster, LLP

(57) ABSTRACT

Proteinaceous antibiotics produced by ruminal bacteria are provided. The diverse group of ruminal bacteria known as Butyrivibrio spp. is a preferred source of such proteinaceous antibiotics. The proteinaceous antibiotics are generally resistant to gastric proteases, exhibit a high level of hydrophobicity, are effective to inhibit growth of target organisms under anaerobic conditions, are ineffective in aerobic conditions, and have a molecular weight of less than about 5 kDa. Also provided are methods for identifying ruminal bacteria which produce such proteinaceous antibiotics, and methods for producing the proteinaceous antibiotics.

8 Claims, 15 Drawing Sheets

OTHER PUBLICATIONS

Barefoot et al., "Antibiosis revisited: Bacteriocins produced by dairy starter cultures" *J. Dairy Sci.* (1993) 76:2366–2379.

Klaenhammer, "Genetics of bacteriocins produced by lactic acid bacteria" *FEMS Microbiol. Rev.* (1993) 12:39–85.

Laukova et al., "Antimicrobial spectrum of bacteriocin–like substances produced by rumen *staphylococci*" *Folia Microbiol.* (1993) 38(1):74–76.

Chikindas et al., "Pediocin PA–1, a bacteriocin from *Pediococcus acidilactici* PAC1.0, forms hydrophilic pores in the cytoplasmic membrane of target cells" *Appl. Env. Microbiol.* (1993) 59(11):3577–3584.

Miranda et al., "Purification and partial characterization of a bacteriocin isolated from *Bacteroides ovatus* H47" *Can. J. Microbiol.* (1993) 39:169–174.

Odenyo et al., "The use of 16S rRNA–targeted oligonucleotide probes to study competition between ruminal fibrolytic bacteria: Development of probes for Ruminococcus species and evidence for bacteriocin production" *Appl. Env. Microbiol.* (1994) 60(10):3688–3696.

Wallace, "Ruminal microbiology, biotechnology, and ruminant nutrition: Progress and problems" *J. Anim. Sci.* (1994) 72:2992–3003.

Jack et al., "Bacteriocins of gram–positive bacteria" *Microbiol. Rev.* (1995) 59(2):171–200.

Abee, "Pore–forming bacteriocins of gram–positive bacteria and self–protection mechanisms of producer organisms" *FEMS Microbiology Lett.* (1995) 129:1–10.

Kalmokoff et al., "Bacteriocin production among isolates of the rumen bacterium" *Abstracts of the 95th General Meeting of the American Society for Microbiology*(1995) Session 42:Abstract 1–11.

Caldwell et al., "Medium without rumen fluid for nonselective enumeration and isolation of rumen bacteria" *Appl. Microbiol.* (1996) 14:794–801.

Forster et al., "Phylogenetic relationships amongst butyrivibrio–like isolates of rumen bacteria and the design of probes for determinative and community structure studies in the rumen" *Abstracts—Conference on Rumen Function-*(Nov. 14–16, 1995) Chicago, Illinois, 23:47 (Abstract No. 81).

Forster et al., "Group–specific 16S rRNA hybridization probes for determinative and community structure studes of *Butyrivibrio fibrisolvens* in the rumen"*Appl. Env. Microbiol.* (1997) 63(4):1256–1260.

Beard et al., "A Stable and Efficient Transformation System for *Butyrivibrio fibrisolvens* OB156," Current Microbiology (1995) 30(2):105–109.

Hefford et al., "The Complete Nucleotide Sequence of a Small Cryptic Plasmid from a Rumen Bacterium of the Genus Butyrivibio," Plasmid (1993) 29(1): 63–69.

Kobayashi et al., "Analysis of the sequence of a new cryptic plasmid, pRJF2, from a rumen bacterium of the genus butyrivibio: Comparison with other butyrivibio plasmids and application in the development of a cloning vector," FEMS Microbiology Letters (1995) 130:137–143.

* cited by examiner

FIG. 1A

PRODUCERS

| STRAIN | ISOLATED FROM | SOURCE |
|---|---|---|
| ACTF2 | OVINE RUMEN (SOUTH AFRICA) | M. A. COTTA (USA) (P. A. HENNING) |
| AR10 | OVINE RUMEN (AUSTRALIA) | K. GREGG (AUSTRALIA) |
| AR73 | OVINE RUMEN (AUSTRALIA) | K. GREGG (AUSTRALIA) |
| ATCC 19171 | BOVINE RUMEN | AMERICAN TYPE CULTURE COLLECTION |
| ATCC 29175 | HUMAN FECES | AMERICAN TYPE CULTURE COLLECTION |
| CF3 | OVINE CECUM (OHIO, USA) | M. A. COTTA (USA) (B. A. DEHORITY) |
| GS111 | ANAEROBIC REACTOR (FLORIDA, USA) | M. A. COTTA (USA) (L. O. INGRAM) |
| NOR37 | BOVINE RUMEN (UK) | M. A. COTTA (USA) (M. SHARPE) |
| OB156 | DEER RUMEN | LAB ISOLATE |
| OB192 | DEER RUMEN | LAB ISOLATE |
| OB194 | DEER RUMEN | LAB ISOLATE |
| OB235 | BOVINE RUMEN | LAB ISOLATE |
| OB236 | BOVINE RUMEN | LAB ISOLATE |
| OB248 | BOVINE RUMEN | LAB ISOLATE |
| OB251 | BOVINE RUMEN | LAB ISOLATE |
| OR35 | BOVINE RUMEN | LAB ISOLATE |
| OR76 | BOVINE RUMEN | LAB ISOLATE |
| OR77 | BOVINE RUMEN | LAB ISOLATE |
| OR78 | BOVINE RUMEN | LAB ISOLATE |
| OR79 | BOVINE RUMEN | LAB ISOLATE |
| OR84 | BOVINE RUMEN | LAB ISOLATE |
| UC12254 | BOVINE RUMEN (MICHIGAN, USA) | M. A. COTTA (USA) (S. KOTARSKI) |
| W1 | BISON RUMEN (NEBRASKA) | M. A. COTTA (USA) (V. VAREL) |
| X10C34 | OVINE RUMEN (SOUTH AFRICA) | M. A. COTTA (USA) (N. O. VAN GYLSWYK) |

FIG. 1B

NON-PRODUCERS

| STRAIN | ISOLATED FROM | SOURCE |
|---|---|---|
| AR27 | OVINE RUMEN (AUSTRALIA) | C. WARE (AUSTRALIA) |
| Bu49 | BOVINE RUMEN | G. P. HAZLEWOOD (GREAT BRITAIN) |
| H10b | BOVINE RUMEN (USA) | M. A. COTTA (USA) (B. A. DEHORITY) |
| H10b(OR2) | BOVINE RUMEN (USA) | B. A. DEHORITY (USA) |
| OB143 | DEER RUMEN | LAB ISOLATE |
| OB145 | DEER RUMEN | LAB ISOLATE |
| OB146 | DEER RUMEN | LAB ISOLATE |
| OB148 | DEER RUMEN | LAB ISOLATE |
| OB149 | DEER RUMEN | LAB ISOLATE |
| OB150 | DEER RUMEN | LAB ISOLATE |
| OB153 | DEER RUMEN | LAB ISOLATE |
| OB155 | DEER RUMEN | LAB ISOLATE |
| OB157 | DEER RUMEN | LAB ISOLATE |
| OB189 | DEER RUMEN | LAB ISOLATE |
| OB232 | BOVINE RUMEN | LAB ISOLATE |
| OB237 | BOVINE RUMEN | LAB ISOLATE |
| OB244 | BOVINE RUMEN | LAB ISOLATE |
| OB247 | BOVINE RUMEN | LAB ISOLATE |
| OB249 | BOVINE RUMEN | LAB ISOLATE |
| OB250 | BOVINE RUMEN | LAB ISOLATE |
| OR36 | BOVINE RUMEN | LAB ISOLATE |
| OR37 | BOVINE RUMEN | LAB ISOLATE |
| OR38 | BOVINE RUMEN | LAB ISOLATE |
| OR85 | BOVINE RUMEN | LAB ISOLATE |
| PI-7 | OVINE RUMEN | G. P. HAZLEWOOD (GREAT BRITAIN) |

FIG. 2A

|  | 5 | 15 | 25 | 35 | 45 |
|---|---|---|---|---|---|
| *OB244* | CA--TGCAAG | TCGAACGGAG | ATTAGACGCT | G-ACGAGACT | TCGGTCAAAT |
| *OB250* | CACATGCAAG | TCGAACGGAT | TTTGCTCGCT | GCA-GAGACT | TCGGTCGAAG |
| *ACTF2* | CACATGCAAG | TCGAACGGAG | -TTATTCGCT | G-ATGAAGCT | TCGGCAGATT |
| *AR10_OR433* | CACATGCAAG | TCGAACGGAG | AATTTACGCT | G-ATGAAGCT | TCGGCAGATT |
| *ATCC_19171* | -ACATGCAAG | TCGAACGGAG | -TTATTCGCT | G-ATGAAGCT | TCGGCAGAAT |
| *ATCC_29175* | CACATGCAAG | TCGAACGAAG | -CACTTCATA | AAGCTTGCTT | TAAGAAG--- |
| *OB248* | CACATGCAAG | TCGAACGGAG | ATATAACGCT | GCATGAGACT | TCGGTCAAAG |
| *OB251* | CACATGCAAG | TCGAACGGAG | TTTACTCGCT | G-ATGAAGCT | TCGGCAGAAT |
| *X10C34* | CACATGCAAG | TCGAACGGAG | ATTAGACGCT | G-ACGAGACT | TCGGTCAAAT |
| *H10b* | CACATGCAAG | TCGAACGAAG | -CAATTTCTT | ACG-ATCCCT | TCGGGGTGAC |
| *OR2_H10b* | CACATGCAAG | TCGAACGAAG | -CAACTTATT | ACG-ATCCCT | TCGGGGTGAC |
| *OR85* | CACATGCAAG | TCGAACGAAG | -CAATTTCT | ACG-ATCCTT | TCGGGGTGAC |
| *AR73_OR435* | CACATGCAAG | TCGAACGAAG | -CAATTTCT | ACG-ATCCCT | TCGGGGTGAC |
| *CF3* | CACATGCAAG | TCGAACGAAG | -CAATTTCTT | ACG-ATCCCT | TCGGGGTGAC |
| *GSIII* | CACATGCAAG | TCGAACGAAG | -CAATTTCC | ACG-ATCCCT | TCGGGGTGAC |
| *NOR37* | CACATGCAAG | TCGAACGAAG | -CAATTTCT | ACG-ATCCCT | TCGGGGTGAC |
| *OB236* | CACATGCAAG | TCGAACGAAG | -CAATTTCT | ACG-ATCCCT | TCGGGGTGAC |
| *OR76* | CACATGCAAG | TCGAACGAAG | -CAATTTCT | ACG-ATCCCT | TCGGGGTGAC |
| *OR77* | CACATGCAAG | TCGAACGAAG | -CAATTTCT | ACG-ATCCTT | TCGGGGTGAC |
| *OR78* | CACATGCAAG | TCGAACGAAG | -CAATTTCT | ACG-ATCCTT | TCGGGGTGAC |
| *OR79* | CACATGCAAG | TCGAACGAAG | -CAATTTCT | ACG-ATCCCT | TCGGGGTGAC |
| *OR84* | CACATGCAAG | TCGAACGAAG | -CAATTTCT | ACG-ATCCTT | TCGGGGTGAC |
| *E14_OR392* | C--ATGCAAG | TCGAACGAAG | -CAATTTCT | ACG-ATCCTT | TCGGGGTGAC |
| *AR27_OR434* | CACATGCAAG | TCGAACGAAG | -CAATTATC | ACG-ATCCTT | TCGGGGTGAC |
| *49_OR107* | CACATGCAAG | TCGAACGAAG | -CAGTTTATC | ACG-ATCCCT | TCGGGGTGAC |
| *OB232* | -ACATGCAAG | TCGAACGAAG | -CAACTTATT | ACG-ATCCCT | TCGGGGTGAC |
| *OR36* | CACATGCAAG | TCGAACGAAG | -CAACTTATT | ACG-ATCCCT | TCGGGGTGAC |
| *OR37* | CACATGCAAG | TCGAACGAAG | -CAACTTATT | ACG-ATCCCT | TCGGGGTGAC |
| *OR38* | CACATGCAAG | TCGAACGAAG | -CAACTTATT | ACG-ATCCCT | TCGGGGTGAC |
| *PI-7_OR106* | CACATGCAAG | TCGAACXAAG | -CAACTTATT | ACG-ATCCCT | TCGGGGTGAC |
| *OR35* | CACATGCAAG | TCGAACGAAG | -CAACTTATT | ACG-ATCCCT | TCGGGGTGAC |
| *UC12254* | CACATGCAAG | TCGAACGAAG | -CAGTTTATC | ACG-ATCCCT | TCGGGGTGAC |
| *VV1* | CACATGCAAG | TCGAACGAAG | -CAGTTTATC | ACG-ATCCCT | TCGGGGTGAC |
| *OB143* | CACATGCAAG | TCGAACGAAG | -CATTTACTT | ACG-ATCCCT | TCGGGGTGAC |
| *OB148* | CACATGCAAG | TCGAACGAAG | -CATTTACTT | ACG-ATCCCT | TCGGGGTGAC |
| *OB149* | CACATGCAAG | TCGAACGAAG | -CATTTACTT | ACG-ATCCCT | TCGGGGTGAC |
| *OB150* | CACATGCAAG | TCGAACGAAG | -CATTTACTT | ACG-ATCCCT | TCGGGGTGAC |
| *OB153* | CACATGCAAG | TCGAACGAAG | -CATTTACTT | ACG-ATCCCT | TCGGGGTGAC |
| *OB155* | CACATGCAAG | TCGAACGAAG | -CATTTACTT | ACG-ATCCCT | TCGGGGTGAC |
| *OB157* | CACATGCAAG | TCGAACGAAG | -CATTTACTT | ACG-ATCCCT | TCGGGGTGAC |
| *OB189* | CACATGCAAG | TCGAACGAAG | -CATTTACTT | ACG-ATCCCT | TCGGGGTGAC |
| *OB156* | CACATGCAAG | TCGAACGAAG | -CATTTACTT | ACG-ATCCCT | TCGGGGTGAC |
| *OB192* | CACATGCAAG | TCGAACGAAG | -CATTTACTT | ACG-ATCCCT | TCGGGGTGAC |

FIG. 2B

|  | 55 | 65 | 75 | 85 | 95 |
|---|---|---|---|---|---|
| OB244 | CTTGTTTA-A | TCTTAGTGGC | GGACGGGTGA | GTAACGCGTG | GGCAACCTGC |
| OB250 | CTTGAGTA-A | AGTTAGTGGC | GGACGGGTGA | GTAACGCGTG | GGCAACCTGC |
| ACTF2 | CTTGAATA-A | -CTTAGTGGC | GGACGGGTGA | GTAACGCGTG | GGTAACCTGC |
| AR10_OR433 | CTTGTAAA-T | TCTTAGTGGC | GGACGGGTGA | GTAACGCGTG | GGCAACCTGC |
| ATCC_19171 | CTTGAATA-A | -CTTAGTGGC | GGACGGGTGA | GTAACGCGTG | GGTAACCTGC |
| ATCC_29175 | -------T-G | ACTTAGTGGC | GGACGGGTGA | GTAACGCGTG | GGTAACCTGC |
| OB248 | CTTGTTGT-A | TCTTAGTGGC | GGACGGGTGA | GTAACGCGTG | GGCAACCTGC |
| OB251 | CTTGAGTA-A | ACTTAGTGGC | GGACGGGTGA | GTAACGCGTG | GGCAACCTGC |
| X10C34 | CTTGTTTA-A | TCTTAGTGGC | GGACGGGTGA | GTAACGCGTG | GGCAACCTGC |
| H10b | GAGTTATT-G | ACTGAGTGGC | GGACGGGTGA | GTAACGCGTG | GGTAACCTGC |
| OR2_H10b | GAGTTATT-G | ACTGAGTGGC | GGACGGGTGA | GTAACGCGTG | GGTAACCTGC |
| OR85 | GGATTATT-G | ACTGAGTGGC | GGACGGGTGA | GTAACGCGTG | GGTAACCTAC |
| AR73_OR435 | GGATTATT-G | ACTGAGTGGC | GGACGGGTGA | GTAACGCGTG | GGTAACCTAC |
| CF3 | GAGATATT-G | ACTGAGTGGC | GGACGGGTGA | GTAACGCGTG | GGTAACCTGC |
| GSIII | GGATTATT-G | ACTGAGTGGC | GGACGGGTGA | GTAACGCGTG | GGTAACCTAC |
| NOR37 | GGATTATT-G | ACTGAGTGGC | GGACGGGTGA | GTAACGCGTG | GGTAACCTAC |
| OB236 | GGATTATT-G | ACTGAGTGGC | GGACGGGTGA | GTAACGCGTG | GGTAACCTAC |
| OR76 | GGATTATT-G | ACTGAGTGGC | GGACGGGTGA | GTAACGCGTG | GGTAACCTAC |
| OR77 | GGATTATT-G | ACTGAGTGGC | GGACGGGTGA | GTAACGCGTG | GGTAACCTAC |
| OR78 | GGATTATT-G | ACTGAGTGGC | GGACGGGTGA | GTAACGCGTG | GGTAACCTAC |
| OR79 | AGATTATT-G | ACTGAGTGGC | GGACGGGTGA | GTAACGCGTG | GGTAACCTAC |
| OR84 | GGATTATT-G | ACTGAGTGGC | GGACGGGTGA | GTAACGCGTG | GGTAACCTAC |
| E14_OR392 | GGATTATT-G | ACTGAGTGGC | GGACGGGTGA | GTAACGCGTG | GGTAACCTAC |
| AR27_OR434 | GATTTATT-G | ACTTAGTGGC | GGACGGGTGA | GTAACGCGTG | GGTAACCTAC |
| 49_OR107 | GATTTACT-G | ACTGAGTGGC | GGACGGGTGA | GTAACGCGTG | GGTAACCTGC |
| OB232 | GATTTGTT-G | ACTGAGTGGC | GGACGGGTGA | GTAACGCGTG | GGTAACCTAC |
| OR36 | GATTTGTT-G | ACTGAGTGGC | GGACGGGTGA | GTAACGCGTG | GGTAACCTGC |
| OR37 | GATTTGTT-G | ACTGAGTGGC | GGACGGGTGA | GTAACGCGTG | GGTAACCTGC |
| OR38 | GATTTGTT-G | ACTGAGTGGC | GGACGGGTGA | GTAACGCGTG | GGTAACCTGC |
| PI-7_OR106 | GATTTGTT-G | ACTGAGTGGC | GGACGGGTGA | GTAACGCGTG | GGTAACCTGC |
| OR35 | GATTTGTT-G | ACTGAGTGGC | GGACGGGTGA | GTAACGCGTG | GGTAACCTGC |
| UC12254 | GATTTACT-G | ACTGAGTGGC | GGACGGGTGA | GTAACGCGTG | GGTAACCTGC |
| VV1 | GATTTACT-G | ACTGAGTGGC | GGACGGGTGA | GTAACGCGTG | GGTAACCTGC |
| OB143 | GAGTTTAT-G | ACTGAGTGGC | GGACGGGTGA | GTAACGCGTG | GGTAACCTAC |
| OB148 | GAGTTAAT-G | ACTGAGTGGC | GGACGGGTGA | GTAACGCGTG | GGTAACCTAC |
| OB149 | GAGTTAAT-G | ACTGAGTGGC | GGACGGGTGA | GTAACGCGTG | GGTAACCTAC |
| OB150 | GAGTTAAT-G | ACTGAGTGGC | GGACGGGTGA | GTAACGCGTG | GGTAACCTAC |
| OB153 | GAGTTTAT-G | ACTGAGTGGC | GGACGGGTGA | GTAACGCGTG | GGTAACCTAC |
| OB155 | GAGTTTAT-G | ACTGAGTGGC | GGACGGGTGA | GTAACGCGTG | GGTAACCTAC |
| OB157 | GAGTTTAT-G | ACTGAGTGGC | GGACGGGTGA | GTAACGCGTG | GGTAACCTAC |
| OB189 | GAGTTTAT-G | ACTGAGTG-C | GGACGGGTGA | GTAACGCGTG | GGTAACCTAC |
| OB156 | GAGTTAAT-G | ACTGAGTGGC | GGACGGGTGA | GTAACGCGTG | GGTAACCTAC |
| OB192 | GAGTTTAT-G | ACTGAGTGGC | GGACGGGTGA | GTAACGCGTG | GGTAACCTAC |

FIG. 2C

|  | 105 | 115 | 125 | 135 | 145 |
|---|---|---|---|---|---|
| OB244 | CTCATACTGG | GGGATAACAG | TTGGAAACGA | CTGTTAATAC | CGCATAAGXG |
| OB250 | CTCATACTGG | GGGATAACAG | TTGGAAACGA | CTGTTAATAC | CGCATAAGCG |
| ACTF2 | CTCATACAGG | GGGATAGCAG | TTGGAAACGA | CTGATAACAC | CGCATAAGCG |
| AR10_OR433 | CTCATACTGG | GGGATAACAG | CTGGAAACGA | CTGTTAATAC | CGCATAAGCG |
| ATCC_19171 | CTCATACAGG | GGGATAGCAG | TTGGAAACGA | CTGATAACAC | CGCATAAGCG |
| ATCC_29175 | CTTACACAGG | GGGATAACAG | TTAGAAATGA | CTGCTAATAC | CGCATAAAAC |
| OB248 | CTCATACTGG | GGGATAACAG | TTGGAAACGG | CTGTTAATAC | CGCATAAGCG |
| OB251 | CTCATACTGG | GGGATAGCAG | TTGGAAACGA | CTGATAATAC | CGCATAAGCG |
| X10C34 | CTCATACTGG | GGGATAACAG | TTGGAAACGA | CTGTTAATAC | CGCATAAGCG |
| H10b | CTTGTACAGG | GGGACAACAG | TTGGAAACGA | CTGCTAATAC | CGCATAAGCG |
| OR2_H10b | CTTGTACAGG | GGGACAACAG | TTGGAAACGA | CTGCTAATAC | CGCATAAGCG |
| OR85 | CTTGTACAGG | GGGACAACAG | TTGGAAACGA | CTGCTAATAC | CGCATAAGCG |
| AR73_OR435 | CTTGTACAGG | GGGACAACAG | TTGGAAACGA | CTGCTAATAC | CGCATAAGCG |
| CF3 | CTTGTACAGG | GGGACAACAG | TTGGAAACGA | CTGCTAATAC | CGCATAAGCG |
| GSIII | CTTGTACAGG | GGGACAACAG | TTGGAAACGA | CTGCTAATAC | CGCATAAGCG |
| NOR37 | CTTGTACAGG | GGGACAACAG | TTGGAAACGA | CTGCTAATAC | CGCATAAGCG |
| OB236 | CTTGTACAGG | GGGACAACAG | TTGGAAACGA | CTGCTAATAC | CGCATAAGCG |
| OR76 | CTTGTACAGG | GGGACAACAG | TTGGAAACGA | CTGCTAATAC | CGCATAAGCG |
| OR77 | CTTGTACAGG | GGGACAACAG | TTGGAAACGA | CTGCTAATAC | CGCATAAGCG |
| OR78 | CTTGTACAGG | GGGACAACAG | TTGGAAACGA | CTGCTAATAC | CGCATAAGCG |
| OR79 | CTTGTACAGG | GGGACAACAG | TTGGAAACGA | CTGCTAATAC | CGCATAAGCG |
| OR84 | CTTGTACAGG | GGGACAACAG | TTGGAAACGA | CTGCTAATAC | CGCATAAGCG |
| E14_OR392 | CTTGTACAGG | GGGACAACAG | TTGGAAACGA | CTGCTAATAC | CGCATAAGCG |
| AR27_OR434 | CTTGTACAGG | GGGACAACAG | TTGGAAACGA | CTGCTAATAC | CGCATAAGCG |
| 49_OR107 | CTTGTACAGG | GGGACAACAG | TTGGAAACGA | CTGCTAATAC | CGCATAAGCG |
| OB232 | CTTGTACAGG | GGGACAACAG | TTGGAAACGA | CTGCTAATAC | CGCATAAGCG |
| OR36 | CTTGTACAGG | GGGACAACAG | TTGGAAACGA | CTGCTAATAC | CGCATAAGCG |
| OR37 | CTTGTACAGG | GGGACAACAG | TTGGAAACGA | CTGCTAATAC | CGCATAAGCG |
| OR38 | CTTGTACAGG | GGGACAACAG | TTGGAAACGA | CTGCTAATAC | CGCATAAGCG |
| PI-7_OR106 | CTTGTACAGG | GGGACAACAG | TTGGAAACGA | CTGCTAATAC | CGCATAAGCG |
| OR35 | CTTGTACAGG | GGGACAACAG | TTGGAAACGA | CTGCTAATAC | CGCATAAGCG |
| UC12254 | CTTGTACAGG | GGGACAACAG | TTGGAAACGA | CTGCTAATAC | CGCATAAGCG |
| VV1 | CTTGTACAGG | GGGACAACAG | TTGGAAACGA | CTGCTAATAC | CGCATAAGCG |
| OB143 | CTTATACAGG | GGGACAACAG | TTGGAAACGA | CTGCTAATAC | CGCATAAGCG |
| OB148 | CTTATACAGG | GGGACAACAG | TTGGAAACGA | CTGCTAATAC | CGCATAAGCG |
| OB149 | CTTATACAGG | GGGACAACAG | TTGGAAACGA | CTGCTAATAC | CGCATAAGCG |
| OB150 | CTTATACAGG | GGGACAACAG | TTGGAAACGA | CTGCTAATAC | CGCATAAGCG |
| OB153 | CTTATACAGG | GGGACAACAG | TTGGAAACGA | CTGCTAATAC | CGCATAAGCG |
| OB155 | CTTATACAGG | GGGACAACAG | TTGGAAACGA | CTGCTAATAC | CGCATAAGCG |
| OB157 | CTTATACAGG | GGGACAACAG | TTGGAAACGA | CTGCTAATAC | CGCATAAGCG |
| OB189 | CTTATACAGG | GGGA-AACAG | TTGGAAACGA | CTGCTAATAC | CGCATAAGCG |
| OB156 | CTTATACAGG | GGGACAACAG | TTGGAAACGA | CTGCTAATAC | CGCATAAGCG |
| OB192 | CTTATACAGG | GGGACAACAG | TTGGAAACGA | CTGCTAATAC | CGCATAAGCG |

FIG. 2D

| | 155 | 165 | 175 | 185 | 195 |
|---|---|---|---|---|---|
| OB244 | CACAGAGTCG | CATGACTCAG | TGTGAAAAAC | TCCGGTGGTA | TGAGATGGGC |
| OB250 | XACAGAGTCG | CATGACTCAG | TGTGAAAAAC | TCCGGTGGTA | TGAGATGGGC |
| ACTF2 | CACAGTATCG | CATGATACAG | TGTGAAAATA | TTTATAGGTA | TGAGATGGAC |
| AR10_OR433 | CACGGTATCG | CATGATACAG | TGTGAAAAAC | TCCGGTGGTA | TGAGATGGGC |
| ATCC_19171 | CACAGTGTCG | CATGACACAG | TGTGAAAATA | TTTATAGGTA | TGAGATGGAC |
| ATCC_29175 | AGCAGAGTCG | CATGACTCAA | CTGTCAAAGA | TTTATCGGTG | TAAGATGGAC |
| OB248 | CACAGAGTCG | CATGACTCAG | TGTGAAAAAC | TCCGGTGGTA | TGAGATGGGC |
| OB251 | XACGGTATCG | CATGATACAG | TGTGAAAAAC | TCCGGTGGTA | TGAGATGGGC |
| X10C34 | CACAGAGTCG | CATGACTCAG | TGTGAAAAAC | TCCGGTGGTA | TGAGATGGGC |
| H10b | CACAGTATCG | CATGGTACAG | TGTGAAAAGT | TTTTTCGGTA | CAAGATGGAC |
| OR2_H10b | CACAGTATCG | CATGGTACAG | TGTGAAAAGT | TTTTTCGGTA | CAAGATGGAC |
| OR85 | CACAGCATCG | CATGATGCAG | TXTGAAAAGT | TTTTTCGGTA | CAAGATGGAC |
| AR73_OR435 | CACAGCATCG | CATGATGCAG | TGTGAAAAGT | TTTTTCGGTA | CAAGATGGAC |
| CF3 | CACAGCATCG | CATGATGCAG | TGTGAAAAGT | TTTTTCGGTA | CAAGATGGAC |
| GSIII | CACAGCATCG | CATGATGCAG | TGTGAAAAGT | TTTTTCGGTA | CAAGATGGAC |
| NOR37 | CACAGCATCG | CATGATGCAG | TGTGAAAAGT | TTTTTCGGTA | CAAGATGGAC |
| OB236 | CACAGCATCG | CATGATGCAG | TGTGAAAAGT | TTTTTCGGTA | CAAGATGGAC |
| OR76 | XACAGCATCG | CATGATGCAG | TXTGAAAAGT | TTTTTCGGTA | CAAGATGGAC |
| OR77 | CACAGCATCG | CATGATGCAG | TGTGAAAAGT | TTTTTCGGTA | CAAGATGGAC |
| OR78 | CACAGCATCG | CATGATGCAG | TXTGAAAAGT | TTTTTCGGTA | CAAGATGGAC |
| OR79 | XACAGCATCG | CATGATGCAG | TGTGAAAAGT | TTTTTCGGTA | CAAGATGGAC |
| OR84 | CACAGCATCG | CATGATGCAG | TXTGAAAAGT | TTTTTCGGTA | CAAGATGGAC |
| E14_OR392 | CACAGCATCG | CATGATGCAG | TGTGAAAAGT | TTTTTCGGTA | CAAGATGGAC |
| AR27_OR434 | CACGGTATCG | CATGATACAG | TGTGAAAAGT | TTTTTCGGTA | CAAGATGGAC |
| 49_OR107 | CACGGAATCG | CATGATTTTG | TGTGAAAAGA | TTTATCGGTA | CAAGATGGAC |
| OB232 | CACAGCTTCG | CATGAAGCAG | TGTGAAAAGT | TATTTCGGTA | CAAGATGGAC |
| OR36 | CACAGCTTCG | CATGAAGTAG | TGTGAAAAGA | TTTTTCGGTA | CAAGATGGAC |
| OR37 | CACAGCTTCG | CATGAAGTAG | TGTGAAAAGA | TTTTTCGGTA | CAAGATGGAC |
| OR38 | CACAGCTTCG | CATGAAGTAG | TGTGAAAAGA | TTTTTCGGTA | CAAGATGGAC |
| PI-7_OR106 | XACAGCTTCG | CATGAAGCAG | TGTGAAAAGT | TATTTCGGTA | CAAGATGGAC |
| OR35 | CACAGCTTCG | CATGAAGTAG | TGTGAAAAGA | TTTTTCGGTA | CAAGATGGAC |
| UC12254 | CACGGAATCG | CATGATTTTG | TGTGAAAAGA | TTTATCGGTA | CAAGATGGAC |
| VV1 | CACGGAATCG | CATGATTTTG | TGTGAAAAGA | TTTATCGGTA | CAAGATGGAC |
| OB143 | CACGATGTTG | CATGACAACG | TGTGAAAAGA | TTTATCGGTA | TAAGATGGAC |
| OB148 | CACGATGTTG | CATGACAACG | TGTGAAAAGA | TTTATCGGTA | TAAGATGGAC |
| OB149 | CACGATGTTG | CATGACAACG | TGTGAAAAGA | TTTATCGGTA | TAAGATGGAC |
| OB150 | CACGATGTTG | CATGACAACG | TGTGAAAAGA | TTTATCGGTA | TAAGATGGAC |
| OB153 | CACGATGTTG | CATGACAACG | TGTGAAAAGA | TTTATCGGTA | TAAGATGGAC |
| OB155 | CACGATGTTG | CATGACAACG | TGTGAAAAGA | TTTATCGGTA | TAAGATGGAC |
| OB157 | CACGATGTTG | CATGACAACG | TGTGAAAAGA | TTTATCGGTA | TAAGATGGAC |
| OB189 | CACAGCTTTG | CATGAAGCGG | TGTGAAAAGA | TTTATCGGTA | TAAGATGGAC |
| OB156 | CACGATGTTG | CATGACAACG | TGTGAAAAGA | TTTATCGGTA | TAAGATGGAC |
| OB192 | CACGATGTTG | CATGACAACG | TGTGAAAAGA | TTTATCGGTA | TAAGATGGAC |

PRODUCING STRAINS (rows) vs INDICATOR STRAINS (columns)

Indicator strain groups:
- III: AR27, Bu49, OB232, OR36, OR37, OR38, PI-7, OR35, UC12254, VV1
- IV: OB143, OB148, OB149, OB150, OB153, OB155, OB157, OB189, OB156, OB192, OB194
- (unlabeled): OB145, OB146, OB237, OB247, OB249, OB235

Producing strain groups (top to bottom): IV (OB235, OB194, OB192, OB156); III (VV1, UC12254, OR35); II (OR391, OR84, OR79, OR78, OR77, OR76, OB236, NOR37, GS111, CF3, AR73); I (X10C34, OB251, OB248, ATCC 29175, ATCC 19171, AR10, ACTF2)

Cell entries: blank (no inhibition), ·, +, ‡, ++, +++, ++++ (increasing inhibition zones).

| Producing \ Indicator | AR27 | Bu49 | OB232 | OR36 | OR37 | OR38 | PI-7 | OR35 | UC12254 | VV1 | OB143 | OB148 | OB149 | OB150 | OB153 | OB155 | OB157 | OB189 | OB156 | OB192 | OB194 | OB145 | OB146 | OB237 | OB247 | OB249 | OB235 |
|---|---|---|---|---|---|---|---|---|---|---|---|---|---|---|---|---|---|---|---|---|---|---|---|---|---|---|---|
| IV OB235 |  | ‡ |  | ‡ | + | ‡ |  |  |  |  | · | ‡ | ‡ |  | ‡ |  | ‡ | ‡ | + |  |  |  |  |  | ‡ |  |  |
| OB194 |  |  |  |  |  |  |  |  |  |  |  |  | + |  |  |  |  |  |  | + |  |  |  |  |  |  |  |
| OB192 |  |  |  | · |  |  |  |  |  |  | + | ‡ | + | ‡ | ‡ | ‡ |  | ‡ |  | + | ‡ |  |  |  |  |  |  |
| OB156 |  |  |  | + |  |  |  |  |  |  |  |  |  |  |  |  |  |  |  |  |  |  |  |  |  |  |  |
| III VV1 |  |  |  | + |  |  |  |  |  |  | · |  |  |  |  |  |  | ‡ | ‡ |  |  |  |  | + |  |  |  |
| UC12254 | ‡ |  | + | + |  |  |  |  |  |  |  | ‡ |  |  |  |  |  | ‡ | + | ‡ |  |  |  |  |  |  |  |
| OR35 |  |  |  |  |  |  |  |  |  |  |  |  |  |  |  | ‡ |  |  |  |  |  |  |  |  |  |  |  |
| II OR391 |  | + |  |  |  |  |  |  |  |  |  |  |  |  |  | + |  |  | ‡ |  |  | · |  |  |  |  |  |
| OR84 | · | ‡ | + | + | + | ‡ |  |  |  |  | · | + | · | + | ‡ | ‡ | ‡ | ‡ | ‡ | ‡ | ‡ | · | · | ‡ | + |  |  |
| OR79 | ‡ | ‡ |  |  | ‡ | ‡ | ‡ | ‡ |  |  | ‡ | ‡ | + | ‡ | ‡ | ‡ | ‡ | ‡ | ‡ | ‡ | ‡ | ‡ | ‡ | ‡ | ‡ |  |  |
| OR78 | ‡ | + | · |  | ‡ | ‡ | ‡ |  |  |  | ‡ | ‡ | + | ‡ | ‡ | ‡ | ‡ | ‡ | ‡ | ‡ | ‡ | ‡ | + | ‡ | ‡ |  |  |
| OR77 |  | + | ‡ | + | ‡ | ‡ | + |  |  |  | ‡ | ‡ | ‡ | ‡ | ‡ | ‡ | ‡ | ‡ | ‡ | ‡ | ‡ | · |  | ‡ | ‡ | ‡ |  |
| OR76 |  | + | ‡ | + | ‡ | ‡ | ‡ |  |  |  | ‡ | ‡ | ‡ | ‡ | ‡ | ‡ | ‡ | ‡ | ‡ | ‡ | ‡ | + | ‡ | ‡ | ‡ |  |  |
| OB236 | · |  |  |  |  | ‡ |  |  |  |  | ‡ | ‡ |  |  |  |  |  | + |  | ‡ |  | ‡ | + | ‡ | ‡ |  |  |
| NOR37 |  | + |  |  | + | ‡ | ‡ |  |  |  | · |  |  |  | ‡ |  |  | + | ‡ |  |  |  |  | ‡ |  |  |  |
| GS111 |  | + | ‡ |  | ‡ | + | ‡ | ‡ |  |  | + |  |  |  | ‡ |  |  |  | ‡ | ‡ |  |  |  | ‡ |  |  |  |
| CF3 |  | + | + |  | + | ‡ | + | + | · |  | ‡ |  |  |  | ‡ |  |  |  | ‡ | + |  |  |  | + |  |  |  |
| AR73 | ‡ | + | · |  | ‡ | + | ‡ | + |  |  | ‡ | ‡ | + | ‡ | ‡ | + | ‡ | + | ‡ | ‡ | ‡ |  | + | + | ‡ | + |  |
| I X10C34 |  |  |  | + |  |  |  |  |  |  |  |  |  |  |  |  |  |  |  |  |  |  |  |  |  | ‡ |  |
| OB251 |  |  |  |  |  |  |  |  |  |  |  |  |  |  |  |  | + |  | + | + |  |  |  |  |  |  |  |
| OB248 |  |  |  |  |  |  |  |  |  |  |  |  | ‡ |  | ‡ |  | ‡ | ‡ |  |  |  |  |  |  |  |  |  |
| ATCC 29175 |  |  |  |  |  |  |  |  |  |  | · |  |  |  |  |  | + | + |  |  |  |  |  |  |  |  |  |
| ATCC 19171 |  |  |  |  |  |  | ‡ |  |  |  | · | + | · | + |  |  |  |  | · | · |  |  |  | ‡ |  |  |  |
| AR10 | ‡ | ‡ | + | ‡ |  | + | +++ | ‡ |  |  | +++ | +++ | + | +++ | ‡ | +++ | ‡ | +++ | ‡ | +++ | ‡ | +++ |  | +++ | + | +++ | ‡ |
| ACTF2 |  |  |  | · | + | · |  | · |  |  |  | + |  | ‡ |  |  | ‡ | + |  |  |  |  |  | + |  |  |  |

FIG. 5A

| | Producing Strains | Clostridium clostridiforma ATCC 25537 | Eubacterium ruminantium ATCC 17233 | Lachnospira multiparus D15d | Lachnospira multiparus ATCC 19207 | Lachnospira multiparus D25e | Lachnospira vitulinus ATCC 27783 | Lactobacillus leichmanni ATCC 4797 | Lactobacillus ruminus ATCC 27780 | Megasphaera eledenii B1159 | Ruminococcus albus SY3 | Ruminococcus flavesfaciens OR18 | Ruminococcus flavesfaciens B34b | Ruminococcus flavesfaciens C94 | Selenomonas ruminentium OB268 | Streptococcus bovis ATCC 33317 | Streptococcus bovis B-b-3 |
|---|---|---|---|---|---|---|---|---|---|---|---|---|---|---|---|---|---|
| | OB235 | ‡ | + | | | | | ‡ | | | | | | | | | |
| IV | OB194 | | | | | | | | | | | | ‡ | | | | |
| | OB192 | ‡ | ‡ | + | | + | | ‡ | ‡ | | | | | | | + | |
| | OB156 | | | | | + | | | | | | | | | | | |
| III | VV1 | | | | | | | | | | | ‡ | ‡ | | | | |
| | UC12254 | ‡ | | + | | | | + | | | | ‡ | ‡ | | | | |
| | OR35 | | | | | | | | | | | | | | | | |
| II | OR391 | ‡ | ‡ | ‡ | | | + | | ‡ | | ‡ | | | | + | | |
| | OR84 | ‡ | ‡ | ‡ | + | | + | | ‡ | | ‡ | | ‡ | | + | + | |
| | OR79 | ‡ | ‡ | ‡ | | ‡ | + | | ‡ | | ‡ | | | | + | + | |
| | OR78 | ‡ | ‡ | ‡ | + | | | | ‡ | | ‡ | | | | + | + | |
| | OR77 | ‡ | ‡ | ‡ | | | + | | ‡ | | ‡ | ‡ | | | + | + | |
| | OR76 | ‡ | ‡ | ‡ | + | | | + | ‡ | | ‡ | ‡ | ‡ | | + | + | |
| | OB236 | ‡ | ‡ | ‡ | + | | | | ‡ | | ‡ | ‡ | ‡ | | + | + | |
| | NOR37 | ‡ | ‡ | + | ‡ | + | + | | ‡ | | ‡ | ‡ | | | + | | |
| | GS111 | ‡ | ‡ | ‡ | ‡ | + | + | | ‡ | | ‡ | ‡ | | | + | | |
| | CF3 | ‡ | ‡ | ‡ | + | ‡ | | | ‡ | | ‡ | ‡ | ‡ | | + | | |
| | AR73 | ‡ | ‡ | | ‡ | + | | | ‡ | | ‡ | ‡ | | | + | | |
| I | X10C34 | | | | | | | | + | | + | | | | | | |
| | OB251 | | | | | | | | | | | | | | | | |
| | OB248 | | | | | | | | | | | | | | | | |
| | ATCC 29175 | | | | | | | | | | | | | | | | |
| | ATCC 19171 | ‡ | ‡ | ‡ | | + | | | ‡ | ‡ | | | | | | + | |
| | AR10 | ‡ | ‡ | ‡ | | | + | | ‡ | | | | | | | | |
| | ACTF2 | ‡ | | | | | | | | | | | | | | | |

NON-BUTYRIVIBRIO RUMEN STRAINS
INDICATOR STRAINS

FIG. 5B

| Group | Producing Strain | C. perfringene | L. mono 87 | L. mono 89 | L. mono 76 | L. mono 77 | L. mono 106 | L. mono 92 | L. mono 102 | L. mono 90 | L. mono 88 | L. mono 104 | L. mono 86 | L. mono 103 | L. mono 91 | L. mono 78 | L. ivanovii 80 | L. seeligeri 81 | L. innocua 79 | L. murrayi 84 | L. gray 83 | L. welchimeri 82

FIG. 6

PROTEASE TREATMENT

| ISOLATE | Peptidase | Pepsin | Trypsin | Pronase | α-chymotrypsin |
|---|---|---|---|---|---|
| AR10 | - | - | - | + | +/- |
| ATCC 19171 | + | + | - | + | + |
| OB251 | + | - | - | + | + |
| X10-C34 | - | - | + | + | + |
| AR73 | - | - | - | + | + |
| CF3 | - | - | - | - | + |
| GS111 | - | + | + | + | + |
| NOR37 | - | - | - | + | + |
| OB236 | - | - | - | + | + |
| OR76 | - | - | - | + | - |
| OR77 | - | - | - | + | - |
| OR78 | - | - | - | + | - |
| OR79 | +/- | - | - | + | - |
| OR84 | - | - | - | + | - |
| OR391 | - | - | + | + | + |
| OB192 | - | - | + | + | + |
| OB194 | - | - | - | + | - |
| OB235 | + | - | + | + | + |

FIG. 7

| FRACTION | VOLUME (ml) | TOTAL A$_{280}$[1] | TOTAL ACTIVITY[2] | SPECIFIC ACTIVITY[3] | RELATIVE SPECIFIC ACTIVITY | YIELD % |
|---|---|---|---|---|---|---|
| CULTURE SUPERNATANT | 1800 | 10026 | 5.76 × 10$^6$ | 575 | 1 | 100 |
| FRACTION I | 200 | 1020 | 3.20 × 10$^6$ | 3137 | 6 | 55 |
| FRACTION II | 13 | 331 | 2.44 × 10$^6$ | 7372 | 13 | 44 |
| FRACTION III | 1 | 1.04 | 6.24 × 10$^5$ | 6 × 10$^5$ | 1043 | 11 |

[1] Absorbance at 280 nm x total volume (ml)
[2] Activity units / ml x total volume (ml)
[3] Total activity / total absorbance at 280 nm

FIG. 9

| PEAK | MOLE % | ESTIMATED AMINO ACID CONTENT |
|---|---|---|
| Aspartic | 6.56 | 2 |
| Glutamic | 4.66 | 2 |
| Serine | 5.01 | 2 |
| Glycine | 13.15 | 5 |
| Threonine | 7.13 | 3 |
| Alanine | 26.17 | 9 |
| Proline | 3.47 | 1 |
| Tyrosine | 3.36 | 1 |
| Valine | 5.96 | 2 |
| Methionine | 1.54 | 1 |
| Isoleucine | 9.73 | 3 |
| Leucine | 3.88 | 1 |
| Phenylalanine | 6.25 | 2 |
| Lysine | 2.92 | 1 |
| Cysteine | N.D. | N.D. |

Calculated Molecular Weight: 3418

FIG. 10

(M)GIQLAPAXYQDIVNXVAAGXX

BACTERIOCINS PRODUCED BY RUMINAL BACTERIA

CROSS-REFERENCE TO RELATED APPLICATIONS

This application is a §371 of PCT/CA96/00269, filed Apr. 26, 1996, which is a continuation-in-part of U.S. patent application Ser. No. 08/430,957, filed Apr. 28, 1995, now abandoned.

FIELD OF THE INVENTION

This invention relates to bacteriocins produced by ruminal bacteria. In particular, this includes bacteriocins produced by the diverse group of ruminal bacteria known as Butyrivibrio spp.

BACKGROUND OF THE INVENTION

Micro-organisms produce a wide variety of compounds which demonstrate anti-bacterial properties; one group of these compounds, the bacteriocins, consists of bactericidal proteins with a mechanism of action similar to the ionophore antibiotics. Bacteriocins are often active against species which are closely related to the producer. Their widespread occurrence in bacterial species isolated from complex microbial communities (for example, the intestinal tract, the oral or other epithelial surfaces) suggests that bacteriocins may have a regulatory role in terms of population dynamics within bacterial ecosystems.

Bacteriocin production is widespread throughout the Eubacteria, particularly in species occupying niches in complex microbial communities. Bacteriocin production may be important in determining dominance, colonisation and maintenance of continuity in such communities. Although scant information is available concerning the occurrence of bacteriocins in rumen bacteria, it is likely that they will be of considerable importance. The rumen may also be a source of interesting new bacteriocins, with unusual spectra of activity. As such, a survey for ruminal bacteriocin producers and an evaluation of the effects of bacteriocins on the endogenous microbial population may provide useful information in our overall understanding of rumen ecology as well as allowing the identification of new antimicrobial compounds for use in a wide range of applications.

Ruminal bacteriocins may be particularly suitable for applications in ruminant production systems. A wide variety of compounds useful for the manipulation of the microbial ecology of the rumen have been investigated. Among the most effective for gross alteration of the rumen fermentation profile are the ionophore antibiotics. These antibiotics work by selecting against the Gram Positive rumen component. Reduction in this rumen component results in an alteration of the acetate to propionate ratio of fermentation end-products, reduction in methane generation, and a significant increase in the efficiency of the rumen fermentation, as reflected by decreased feed inputs. Furthermore, these agents have application for alteration of both dairy milk fat quantity and quality.

The ratio of acetate to propionate produced in the rumen appears to be the primary determinant of butterfat levels in milk. This ratio is determined by the relative numbers of acetate-producing bacteria and propionate-producing bacteria in the rumen. The ionophore antibiotics used to manipulate the ratio of acetate to propionate producing bacteria in the rumen are produced as fermentation products by micro-organisms (streptomycetes) originally isolated from soils.

Ionophore antibiotics have a history of effective use in meat production systems, but are not presently used in dairy production. Ionophore antibiotics have a number of limitations when used in ruminant production systems. These disadvantages include that:

(a) they are not produced by the rumen bacteria themselves and must be introduced into the rumen repeatedly, (b) they are not proteins and therefore they are not subject to easy modification by genetic engineering and are not easily digested and utilised by the animal like a protein (in fact they may exhibit residue problems), and (c) they do not exhibit a high degree of specificity for their targets and thus they do not provide opportunities for precise control of rumen output.

An important difference between beef and dairy cattle is the potential period of treatment with antibiotics. Antibiotic supplements are generally used for only limited periods of time in beef cattle, whereas the period of treatment in dairy cattle may extend over many years. General experience has shown that the prolonged use of antibiotics eventually leads to the selection of resistant microbial populations, ultimately negating any positive effects from direct supplementation. Furthermore, concerns in regards to contamination of products with antibiotic residues, antibiotic toxicity, and the spreading of multiple drug resistance are also of concern when administering ionophore antibiotics to animals.

Previously characterised bacteriocins are a heterogeneous group of proteinaceous antibiotics, and are found throughout the family of microorganisms known as bacteria. Subject of particular study are those produced by the lactic acid bacteria and food Propionibacter, organisms with wide use throughout the food processing industry. Bacteriocins, produced by these organisms play a role in the control of Gram Positive bacterial contaminants and food borne pathogens.

The lactic acid bacteria ("LAB"), a diverse group of organisms which includes the Lactobacilli, Lactococci, Pediococci, Leuconostoc, and Streptococci, are of particular interest in terms of the widespread occurrence of bacteriocins within the group. These species are in wide use throughout the fermented dairy, food and meat processing industries. Their role in both the preservation and flavour characteristics of foods has been well documented. Most of the bacteriocins produced by this group are active only against other lactic acid bacteria, but several display anti-bacterial activity towards more phylogenetically distant Gram Positive and, under certain conditions, Gram Negative bacteria. Nisin, a bacteriocin produced by Lactococcus lactis with a very wide spectrum of activity, has found use as an additive in the food processing and animal health industries.

To date, approximately 30 bacteriocins from food related AB have been reported (Klaenhammer, 1993), as well as two more in dairy Propionibacter (Barefoot and Nettles, 1993). In the majority of cases, primary characterisation has been based on the source of isolation, spectrum of activity among LAB and food contaminants, sensitivity to gastric proteases and crude estimates of molecular weight. Only a portion of these have been isolated and well characterised in terms of protein and genetic components.

In a recent review, Klaenhammer (1993) classified the LAB-derived bacteriocins known to date into four major groups:

Class I—Lantibiotics: small peptides (<5 kDa) containing the unusual amino acids lanthionine and β-methyl lanthionine. These are of particular interest in that they have very broad spectra of activity relative to other bacteriocins.

Examples include Nisin, Nisin Z, carnocin U 149, lacticin 481 and lactocin 5.

Class II—Small non-lanthionine containing peptides: a heterogeneous group of small peptides (<10 kDa). This group includes peptides active against Lysteria spp.

Class III—Large Heat Labile Proteins: >30 kDa, Helveticin is the only one characterised to date.

Class IV—Complex bacteriocins: proteins containing additional moieties (lipids, carbohydrates). None have yet been purified.

Both Class III and IV generally would be expected to have very narrow spectra of activity.

The primary target of the LAB bacteriocins in susceptible strains appears to be the cell membrane. Effects on target cells include membrane depolarisation, efflux of various ions and cellular constituents, and in some cases cell lysis. All are thought to result from the formation by the bacteriocins of membrane pores. Recent work (Bruno and Montville, 1993) suggests that the primary effect is the dissipation of Proton Motive Force (PMF) in a concentration-dependent fashion. In Gram Positive bacteria, PMF plays a fundamental role in energy metabolism, and dissipation affects both ATP generation and active transport mechanisms, ultimately leading to cell death. This mechanism of activity is similar to that of the ionophore antibiotics.

Secondary effects such as leaking of cell constituents or cellular lysis occur at much higher bacteriocin concentrations. Cell lysis observed with certain bacteriocins like nisin and pediocin PA-1 is a non-specific effect, likely resulting from the induction of cell-associated autolytic systems by displacement of muramidase enzymes associated with the lipoteichoic acid component of the cell wall by these bacteriocins (Piard and Desmazeaud, 1992).

Bacteriocin-producing strains are normally immune to the action of the bacteriocin they produce, indicating the presence of an immunity mechanism. Identification of these immunity proteins by characterisation of bacteriocin producing non-immune mutants has revealed a number of points.

Firstly, immunity proteins are usually cotranscribed with the bacteriocin structural gene.

Secondly, sequence analysis of the open reading frames assigned to immunity indicate that the gene products have the characteristics of membrane-bound proteins. In fact, expression of the nisin immunity protein (nisI), an externally located lipo-protein, was found to confer resistance in a non-producing strain of *L. lactis* subsp. lactis. (However, recent work on the immunity protein for lactococcin A has shown in this instance the protein may not be membrane bound (Nisen-Meyer et al. 1993)).

Thirdly, evidence from the lactococcin A,B,M producing strain of *L. lactis* indicates that no cross immunity occurs in deletion mutants missing one of the immunity proteins, indicating that immunity is bacteriocin specific. The functional basis of immune mechanisms has yet to be investigated.

Determinations of spectra of activity of these bacteriocin agents have largely been limited to organisms which occur as contaminants in specific food products, and as of yet no reports concerning sensitivities among rumen bacteria have been published.

To date, limited information concerning bacteriocin production within rumen bacterial isolates is available, and no comprehensive survey of rumen Gram Positive bacteria has been reported. Iverson and Mills (1976) surveyed 47 strains of *Streptococcus bovis*, of which fourteen were bacteriocin producers. Based on sensitivity profiles, these could be further divided into 6 groups. However, only one of these producers was of rumen origin. Similarly, Arihara et al. (1993) reported a putative bacteriocin in *S. bovis* ATCC 1388 (which is also not a rumen isolate). No further work beyond protease sensitivity was carried out in either case. However, given the wide occurrence of lantibiotic production among different species of Streptococci, these *S. bovis* bacteriocins may represent new lantibiotics. A putative bacteriocin has also been identified in a single strain of *Ruminococcus albus* (Odenyo et al., 1993).

With the exception of the single isolates of *Ruminococcus albus* (Odenyo et al., 1993) and *Streptococcus bovis* (Iverson and Mills, 1976), little work has been carried out on the occurrence of bacteriocins among rumen isolates. Given the large numbers and diversity of the bacterial population within the rumen, this represents a valuable environment for the isolation of new bacterlocins. Furthermore, the rumen environment contains a high level of proteolytic activity, which should yield new bacteriocins with interesting protease stabilities.

*Butyrivibrio fibrisolvens* represents a major component of the Gram Positive rumen flora. However, the designation as a single species is misleading, as the "species" consists of a large number of diverse isolates that show differences in terms of extra-cellular polysaccharides, antigenicity, proteolytic activity and protein composition of the cellular membrane.

In general, speciation of *Butyrivibrio fibrisolvens* has been based on common features including anaerobiosis, the production of butyric acid as a major metabolic end-product, resistance to Nalidixic acid, and a vibrioid cellular shape (Bryant, 1986). Taxonomic classification of the isolated strains based on comparisons of 16s rRNA sequence, or the DNA sequence of the gene coding for the 16s ribosomal RNA subunit, or SDS gel electrophoresis of soluble proteins is also possible.

Whole cells of *Butyrivibrio fibrisolvens* stain Gram Negative; however, thin section analysis of the cellular envelope has demonstrated that they are in fact Gram Positive, having an unusually thin peptidoglycan layer. 16s rRNA gene sequence analysis has confirmed that Butyrivibrio spp. are in fact closely related to Gram Positive organisms of the Clostridial cluster XIVa (Forster et al., 1995).

Therefore it is desirable to obtain antibiotics that are proteinaceous but gastric protease resistant, that may exhibit a high degree of specificity with respect to the target microorganisms against which they are effective, that are effective as inhibitors of target microorganisms under anaerobic conditions and ineffective in atmospheric conditions, and that are produced in the rumen of ruminants.

Accordingly, many *B. fibrisolvens* isolates from both diverse rumen and geographical sources have been examined for the presence of bacteriocins meeting these requirements. A surprisingly high incidence of bacteriocin production has been observed among these isolates.

SUMMARY OF THE INVENTION

The present invention relates to proteinaceous antibiotics derived from ruminal bacteria, which antibiotics are effective against target microorganisms under anaerobic conditions and ineffective in atmospheric conditions. Further, the proteinaceous antibiotics are hydrophobic, generally resistant to digestion by gastric proteases, may exhibit a greater specificity with respect to the target microorganisms against which they are effective as compared to ionophore antibiotics used as feed additives, and are generally less than 5.0 kDa in size.

The present invention further relates to ruminal isolates capable of producing the aforementioned proteinaceous antibiotics and comprising one or more strains of anaerobic Gram Positive (as determined by thin section and cell envelope structure analysis) microorganisms which have a vibrioid cellular shape, exhibit resistance to Nalidixic acid, and produce butyric acid as a major metabolic end-product. All of the microorganisms conform to the genus Butyrivibrio as currently defined (Bryant 1986). Their relatedness has been confirmed through 16s rRNA gene sequence analysis.

The bacteriocins according to the invention should be useful in ruminant production systems, as alternatives to ionophore antibiotics, for producing improved feed efficiency, reduced methane production, and lower levels of trans-saturated fatty acids in dairy products. The bacteriocins and the ruminal isolates according to the invention should be useful as selective agents for introduction of new or engineered bacterial strains into microbial ecosystems including but not limited to the rumen itself, or as silage inoculants. The ruminal isolates according to the invention may also be useful as probiotic microbial strains (native or transgenic strains).

The bacteriocins, and genetically engineered Butyrivibrio bacteriocins in non-ruminal organisms, may be useful as silage additives or inoculants, as well as food additives, particularly in anaerobic packaging systems (wherein the oxygen sensitive bacteriocin is inactivated upon opening the package thus resulting in no developed resistance to the bacteriocin) to prevent the growth of Gram Positive spoilage bacteria such as Listeria or Clost Heidium.

The bacteriocins may also be useful as antimicrobial agents in animal or human health applications.

BRIEF DESCRIPTION OF DRAWINGS

In drawings which illustrate embodiments of the invention,

FIGS. 1A and B together are a table listing tested Butyrivibrio producer and nonproducer strains (respectively), FIGS. 2A through 2D (SEQ ID NOS:1–43) together are a table listing partial genomic DNA sequences (from positions 1 through 50, 51 through 100, 101 through 150, and 151 through 200, respectively) coding for 16s rRNA from tested Butyrivibrio isolates (SEQ ID NOS:1–43), FIG. 6 is a table listing the sensitivity of the bacteriocin-like activity in eighteen Butyrivibrio isolates to digestion by five different proteases, FIG. 7 is a table showing yield of Butyrivibriocin AR10 at each step during the purification of the bacteriocin, FIG. 9 is a table showing the amino acid analysis of the purified Butyrivibriocin AR10.

FIG. 10 (SEQ ID NO:44) is a partial amino acid sequence of Butyrivibriocin AR10 derived from the N-terminus of the C-terminus peptide fragment generated by CNBr cleavage of Butyrivibriocin AR10 (SEQ ID NO:44).

DETAILED DESCRIPTION OF THE PREFERRED EMBODIMENT

Cultures

Figure 3:
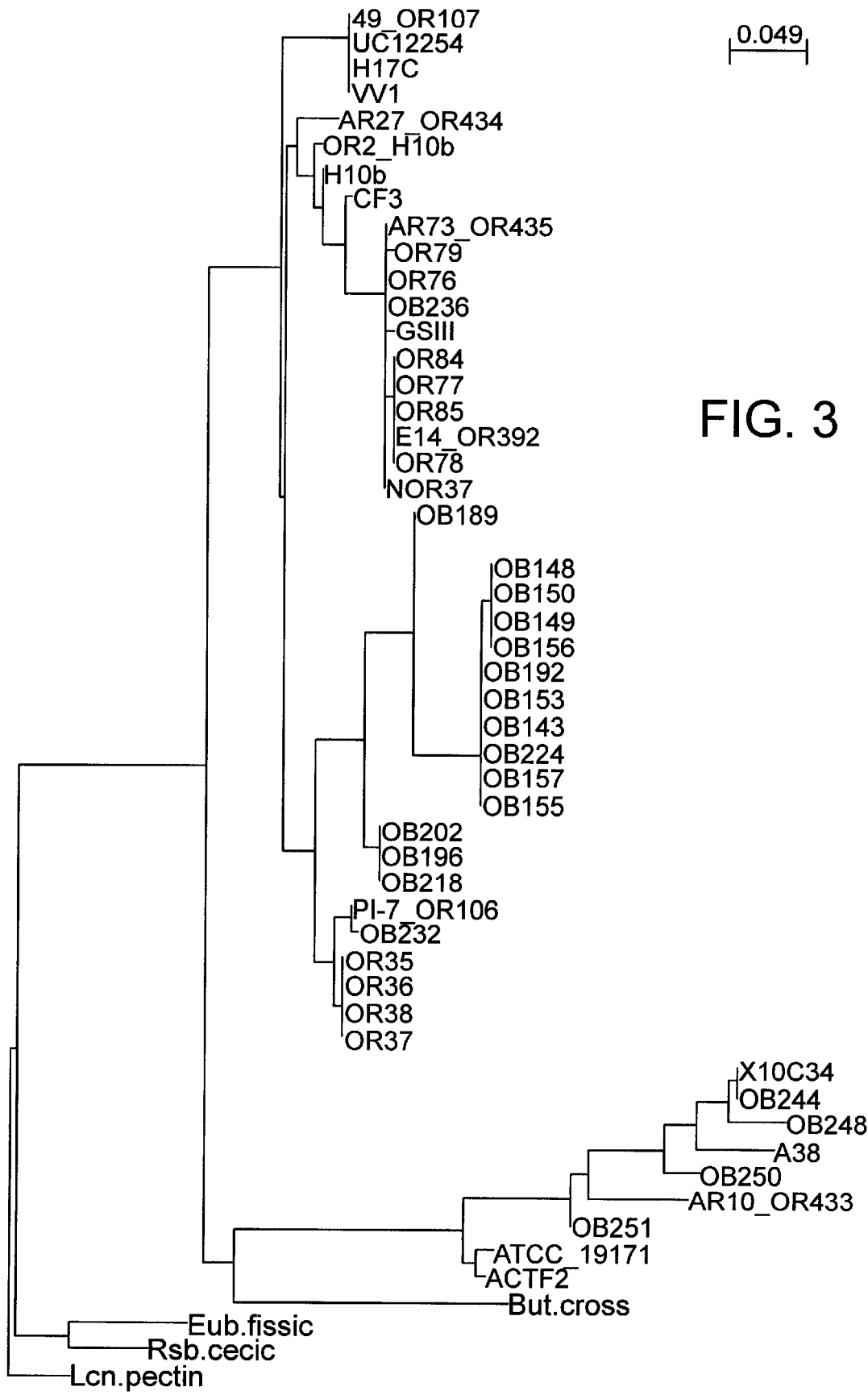
FIG. 3 is a phylogenetic tree depicting phylogenetic relationships of tested Butyrivibrio isolates organised according to relatedness based on analysis of their 16s rRNA gene partial sequences, FIGS. 4A and 4B together are a table listing sensitivities of Butyrivibrio isolates to inhibition by Butyrivibrio isolates producing bacteriocin-like activity, organized in groups I through IV according to relatedness based on analysis of their 16s rRNA gene homology, FIGS. 5A and 5B together are a table listing sensitivities of non-Butyrivibrio bacterial isolates to inhibition by Butyrivibrio isolates producing bacteriocin-like activity, organized in groups I through IV according to relatedness based on analysis of their 16s rRNA gene homology.

The Butyrivibrio isolates tested and their respective sources are listed in FIG. 1. Non-Butyrivibrio rumen isolates tested are listed in FIGS. 5A and 5B. The majority of the strains are from a collection maintained by the Centre for Food and Animal Research, Agriculture and Agri-Food Canada, and span a 15 year collection period. All Butyrivibrio spp. isolates were small rods with varying degrees of vibrioid type shape, were resistant to Nalidixic acid, and produced butyric acid as a major metabolic end-product. Whole cells stained Gram Negative. All of the isolates are related based on 16s rRNA gene sequence analysis as shown in FIGS. 2A through 2D, and FIG. 3. Stock cultures were maintained at −20° C. frozen in glycerol. Routine culturing and testing were carried out using L-10 medium (Caldwell and Bryant, 1966), with the inclusion of glucose, maltose and soluble starch as carbohydrate sources, in either liquid or solid (1% agar) medium. Cultures were grown at 37° C., in an environment consisting of 10% $H_2$ and the balance $CO_2$. For the growth of non-Dutyrivibrio isolates, cellobiose (0.5% w/v) was routinely included within the growth medium.

Production of Inhibitors

Screening of Butyrivibrio spp. for the production of bacteriocin-like activity was carried out using a deferred antagonism method (Tagg et al., 1976). Individual isolates were patched onto square petri dishes (10 cm) containing L-10 agar medium in a grid pattern (nine per plate). Following overnight incubation at 37° C., the plates were removed from the glove box and the growth washed from the surface of the plate using water and a bent glass rod. The washed plates were sterilised by a brief exposure to chloroform (5 min), then the plates were held upright briefly (5–10 min) in a fume hood to allow dissipation of the chloroform residues. The plates were then placed back into the glove box and allowed to re-reduce (4–5 hours). Plates were overlaid with 6.0 ml of overlay agar containing $10^7$ cells from a fresh overnight culture of the test organism. Overlaid plates were incubated overnight at 37° C., after which they were examined for zones of growth inhibition. In this manner, each of the Butyrivibrio isolates was tested against every other isolate.

Zones of growth inhibition were tested for the presence of bacteriophage as follows: a sample of the overlay agar was removed from the zone of clearing using a sterile loop, placed into 1.0 ml of fresh L-10 medium, and gently agitated to allow release of phage particles. The preparation was sterilised by passage through a 0.22 µm filter, and a 10 µl sample was respotted onto a fresh lawn containing the test strain. Following overnight incubation at 37° C., lawns were examined for evidence of bacteriophage (clearing zone or plaques).

Isolates found to produce bacteriocin-like activity using the deferred plating technique were tested for the production of bacteriocin-like activity in liquid cultures. Briefly, following overnight growth in L-10 medium, a 1.0 ml sample of the culture was centrifuged to remove the cells, and a 100 µl aliquot dropped onto a sterile petri dish and sterilised by exposure to shortwave ultraviolet light for a five minute period. Bacteriocin-like activity within the uv-sterilized spent culture fluid was assayed using both a drop test and diffusion well assay (Tagg et al., 1976). All steps were carried out under anerobic conditions in a glove box.

Induction of bacteriocin-like Activity in Liquid Cultures

Semi-defined rumen medium (L-10: Caldwell and Bryant, 1966) is designed for the isolation and enumeration of anaerobes within rumen fluid. Isolates of Butyrivibrio which had previously been shown to demonstrate bacteriocin-like activity as detected by an indirect plating procedure do not produce detectable levels of bacteriocin-like activity in the spent culture fluids when grown within this medium. However, the addition of increased levels of fermentable carbohydrates (2.0% w/v versus 0.2% w/v) resulted in significant improvements in cellular growth with two isolates (*B. fibrisolvens* AR10 and OR73) as well as production of detectable bacteriocin-like activity within sterilised spent culture fluids.

Protease Sensitivity

Protease sensitivity of the bacteriocin-like activity was determined using two methods. The first method was used to assess the proteolytic sensitivities of the inhibitory end-products produced by the various Butyrivibrio isolates. Each specific protease (Peptidase, Pepsin, Trypsin, Pronase and α-Chymotrypsin: sterile stock solutions at 10 mg/ml) was mixed with 6.0 ml of overlay agar (final concentration of 50 µg/ml) and poured over the surface of a washed, chloroform treated deferred assay test plate which had previously been inoculated with the selected producing strains, prepared as above. The control plate overlay contained no added protease. The overlaid plates were incubated at 37° C. for a 4–5 hour period. Following the incubation period, the plates were overlaid with 6.0 ml of agar containing $10^7$ bacteria from a fresh overnight culture of the appropriate indicator. Plates were incubated at 37° C. overnight, and were examined for the elimination or reduction in the zones of inhibition by comparison with control plates which contained no added protease.

Determination of protease sensitivity of bacteriocin-like activity in liquid cultures was carried out as follows: 10 µl of a stock solution (10 mg/ml) of each protease was added to 100 µl of either spent culture medium or the purified bacteriocin, and incubated at 37° C. for 2 hours, after which activity was assessed using a drop test (Tagg et al., 1976). Controls consisted of protease only (1 in 10 dilution) spotted directly onto an overlay containing the indicator organism.

Spectrum of Activity

Non-Butyrivibrio rumen isolates, Listeria spp. and Clostridium spp. isolates were tested for sensitivity towards the bacteriocin-like activity produced by the Butyrivibrio isolates as follows: Producer isolates of Butyrivibrio were patched onto a square plate in a grid pattern (eight isolates). A non-bacteriocin-producing Butyrivibrio isolate was used as a negative control, and was patched onto each plate (ninth position of the grid). This control was used to confirm that inhibition was the result of the bacteriocin-like activity, rather than a result of inhibition caused by end-products of metabolism. Plates were processed as above (see Production of Inhibitors), and overlaid with 6.0 ml overlay agar containing $10^6$ cells of the target test organism. Following overlaying of the plates, the plates were incubated overnight at 37° C., and then examined for zones of growth inhibition.

Isolation of the Bacteriocin Produced by Butyrivibrio Fibrisolvens AR10

Large scale cultures (2.0 L) used for the isolation of inhibitory activity were grown under stationary conditions at 37° C. using L-10 medium supplemented with additional glucose (2.0% w/v). Bacteriocin activity was monitored throughout the purification as illustrated in FIG. 7. Following completion of the incubation (24 hrs), Tween 20 was added to the cultures to a level of 0.1% (v/v), the culture mixed, and the cells removed by centrifugation (10 min., 10,000×g). Spent culture fluids were precipitated by the addition of solid ammonium sulphate (60 g/100 ml),.and the precipitate collected by centrifugation (30 min, 10,000×g). The resulting pellet was resuspended into 200 ml of distilled water, the insoluble materials removed by centrifugation (30 min., 10,000×g) and the pellet discarded. The majority of inhibitory activity precipitated in the 20–40% ammonia-sulphate cut. This cut was collected as above, and the pellet resuspended into 200 ml distilled water. This is referred to as Fraction I.

Fraction I was mixed with an equal volume of ice cold methanol, and placed at 4° C. overnight. Following overnight incubation, the sample was centrifuged (30 min, 10,000×g) to remove precipitated materials, the pellet was discarded. The supernatant was freeze dried to remove the methanol, resuspended into loo ml dH$_2$O, and centrifuged (30 min, 18,000×g) to remove non-soluble materials. Following centrifugation, the supernatant was washed extensively with distilled water (four volumes) to remove salts using an Amicon stirred cell (100 ml volume) fitted with a 3000 m.w. cut-off ultrafiltration membrane. The sample was concentrated to a final volume of 20 ml, and subjected to high speed centrifugation to remove precipitated materials (60 min., 100,000×g). The resulting pellet was discarded, and the supernatant remaining is referred to as Fraction II. Activity was determined at each point during the purification.

The active component was purified by FPLC (Fast Flow Liquid Chromatography System, Pharmacia) using reverse phase chromatography. All steps were carried out at 4° C. Solvents consisted of dH$_2$O (buffer A) and 2-propanol (buffer B), both of which contained 0.1% trifluoroacetic acid. A 0.5 ml aliquot of the crude bacteriocin preparation containing 0.19 TFA was injected onto a Resource RPC 3.0 ml column (Pharmacia), washed with two column volumes of buffer A, and eluted from the column with a gradient from 100% buffer A to 100% buffer B, at a flow rate of 1.0 ml/minute. The elution was monitored at 206 nm. Collected Ifractions were assayed for inhibitory activity by spot testing, the active fractions were pooled, and the sample was freeze dried in a rotary vacuum centrifuge. The active fraction was redissolved into 0.5 ml of 6M Guanidine-HCl, centrifuged (10 min, 16,000×g), filtered through a 0.22 µm filter, reinjected onto the column and eluted as a single peak as above. Samples were stored at 4° C. in 2-propanol until required.

Screening of Butyrivibrio spp. for bacteriocin-like Activity

Figure 4A:
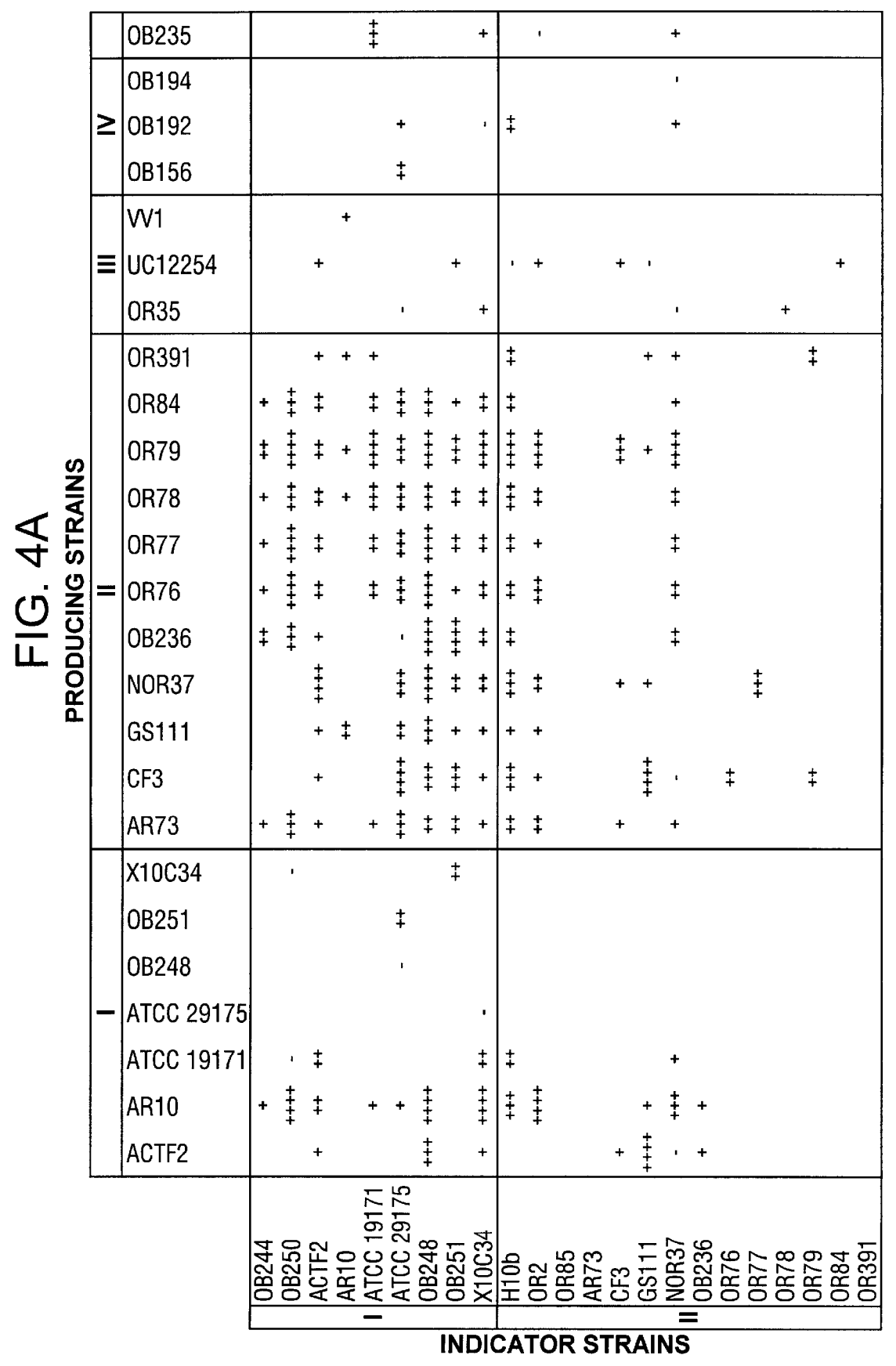

Forty-nine isolates of Butyrivibrio fibrisolvens and one isolate of Butyrivibrio crossotus were screened for inhibitory end-products using a deferred plating procedure (Tagg et al., 1976). Results from this screening are presented in FIGS. 4A and 4B. Twenty-five of the isolates were found to produce activity which to varying degrees inhibited the growth of the additional isolates, while the remaining 25 isolates exhibited no production of inhibitory end-products. Each isolate was tested against all of the other Butyrivibrio isolates in FIG. 1. There was a marked variation in terms of the size of the clearing zone and the degree of clearing among the strains exhibiting the production of inhibitory activity. The intensity of the inhibitory reaction was scored on an arbitrary scale ranging from weak indistinct clearing zones (−) to large (>15 mm) clear inhibition zones (++++).

Overall, inhibitory producing strains were found throughout all four major 16s rRNA homology groups (FIGS. 4A, 4B, 5A, 5B), as well as in *B. fibrisolvens* OB235, a strain falling outside of the four major homology groups. None of the clearing zones was the result of bacteriophage, as replating filter sterilised extracted overlay agar picked from the centre of the clearing zones (see above) did not result in either plaques or clearing zones on fresh overlays (Tagg et al., 1976).

Characteristics of Inhibitory Activity

With the exception of a single strain (*B. fibrisolvens* OR435), no inhibitory activity was detectable in sterilised spent culture fluids from any of the inhibitory producing strains using either a drop test or diffusion well assay. Detection of inhibitory activity in spent culture fluids from *B. fibrisolvens* CR435 was a variable characteristic, and inhibition as detected by spot testing was extremely weak.

In order to overcome the lack of production of the inhibitory end-products in liquid cultures, protease sensitivity of the inhibitory activity was evaluated by the inclusion of each specific protease with the appropriate indicator strain into the overlay agar used in the deferred plating method. Isolates which produced a weak level of inhibitory activity (OB156, VV1, UCI 12254, OR35, OB248, and *B. crossotus* ATCC 29175), could not be evaluated using this procedure. Results are presented in FIG. 6.

With the exception of *B. fibrisolvens* CF3, all of the tested inhibitory end-products were sensitive towards digestion with pronase, but overall, quite resistant towards digestion with gastric peptidases. Identical sensitivity profiles were found among a number of the inhibitors (i.e. AR10, AR73, NOR37, OB236—sensitive to Pronase and α-chymotrypsin only; OR76, OR77, OR78, OR84—sensitive towards α-chymotrypsin; X10-C34, 0B192 and OR391—resistant to peptidase and pepsin only).

Low levels of inhibitory activity extracted from the agar surrounding colonies of *B. fibrisolvens* AR10 and OR79 were detectable by spot testing. In both cases, the inhibitors passed through a membrane with a molecular weight cut-off of 10,000, providing that the extraction was carried out under anaerobic conditions. Exposure of the extracts to the atmosphere resulted in the loss of inhibitory activity. When using the deferred plating technique, short exposure to the atmosphere (i.e. washing off of colonies and sterilisation) did not appear to effect detection of inhibitory activity in any of the isolates, providing that the plates were placed back into the hood and allowed to re-reduce (generally 4–5 hours before plating). However, plates which had been exposed to the atmosphere for longer periods (i.e. overnight), did not display zones of inhibitory activity when overlaid with a sensitive test isolate. These findings suggested that the inhibitors were oxygen sensitive.

Production of bacteriocin-like Activity in *B. fibrisolvens* AR10 and OR79 in Liquid Culture L-10 medium (Caldwell and Bryant, 1966) is a semi-defined medium, and contains no rumen fluid. The medium was designed for the growth and enumeration of a wide variety of rumen isolates. Although all of the tested strains grew in the medium, a large variation was noted among the strains in terms of the quantity of cellular growth. The majority of strains grew poorly in this medium. It was noted that significant improvements in growth resulted from increasing the level of glucose from 0.2 to 2% (w/v). Increased levels of growth resulted in the presence of low levels of protease sensitive inhibitory activity in filter sterilised spent culture fluids in two tested isolates, *B. fibrisolvens* AR10 and OR79.

Purification of Butyrivibriocin AR10

The production of low levels of inhibitory activity could be detected in spent culture fluids from cultures of *B. fibrisolvens* AR10 which contained additional glucose. Further increases in carbohydrate beyond 2% (w/v) had no further effect on enhancing production in liquid culture. As several bacteriocins are known to be cell associated (Jack et al., 1995), bound activity was assayed for by washing pelleted cells with various detergents (Triton X-100, Tween 80, Tween 20). Triton X-100 was found to be very detrimental to the indicator, even at levels less than 0.1% (v/v). However, both Tween 80 and Tween 20 appeared to have no detrimental efLect on the indicator at levels of up to 1.0% (v/v). Significant activity (approximately 50% of total) was found to be cell associated, and extractable using Tween 20 at 0.1% (v/v) In addition, the inclusion of Tween 20 (0.1% v/v) into spent culture fluid, and the subsequent crude, semi-crude and purified bacteriocin prior to assaying for activity, significantly increased activity as determined by spot testing.

Figure 8:
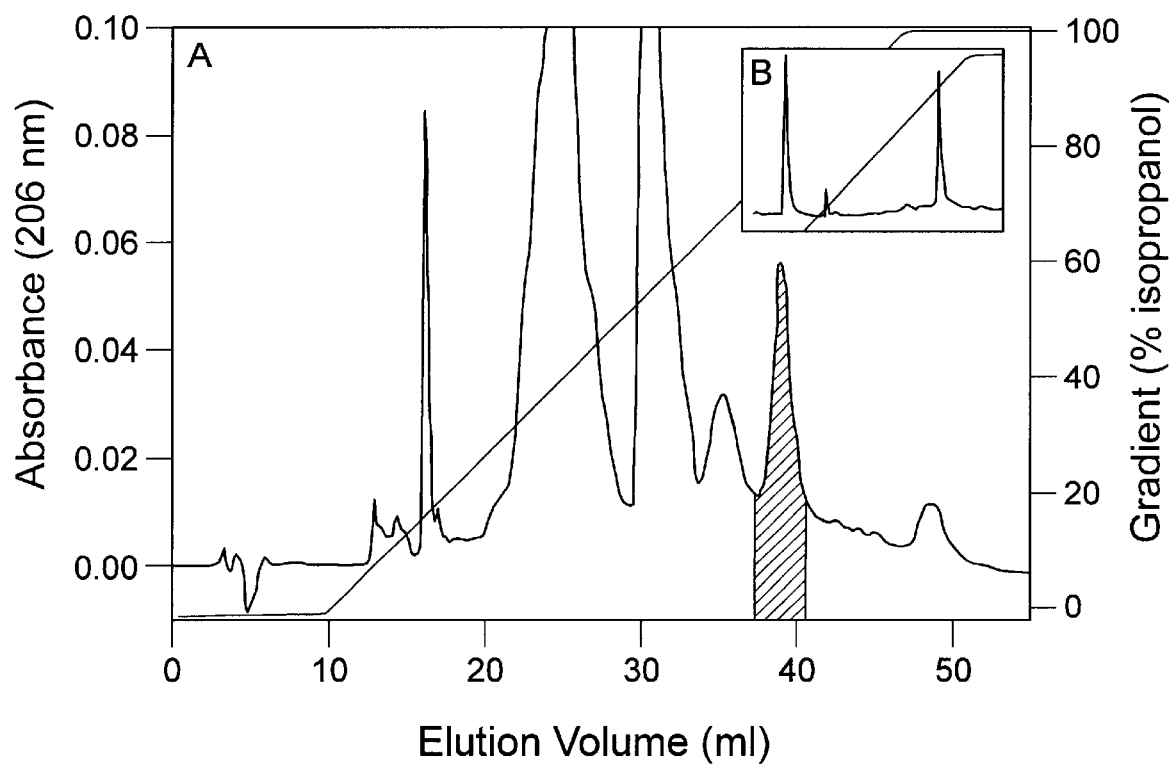
FIG. 8 is a tracing of a reverse phase chromatographic purification of Butyrivibriocin AR10 from a semi-pure crude preparation using reverse phase chromatography, in which the peak corresponding to bacteriocin activity is shaded and in which the inset (B) represents the rechromatography of the active peak.

The inhibitory peptide was isolated from spent culture fluids by a combination of ammonium sulfate precipitation, methanol precipitation, and reverse phase chromatography (FIG. 7). The inhibitory activity was eluted from the column as a single peak quite late into the gradient (80% Buffer B, see FIG. 8). Rerunning of the sample confirmed a composition as a single peak (see FIG. 8, inset).

The purity of the peptide was assessed using Triacine-sodium-dodecyl-sulphate-polyacrylamide gel electrophoresis analysis followed by silver staining. Results indicated that the single peak isolated by reverse phase chromatography consisted of a single peptide. Confirmation of the inhibitory activity of the peptide was confirmed by spot testing. Treatment of the bacteriocin with a-chymotrypsin or pronase prior to sample preparation completely eliminated inhibitory activity. Protease sensitivity of the isolated bacteriocin was identical to the protease sensitivity of the inhibitor produced in the deferred plate test (see above).

Amino Acid Composition and Sequence Analysis

Amino acid analysis of the isolated inhibitory peptide indicated an approximate molecular weight of 3,400. Results of the amino acid analysis are presented in FIG. 9. The N-terminus of the native peptide was blocked towards micro sequence analysis. However, amino acid analysis had indicated the presence of a single methionine within the peptide. Treatment of the peptide with CNBr resulted in the generation of a C-terminus fragment. The sequence of the N-terminus of the C-terminus fragment was derived. A twenty-two amino acid sequence was obtained (FIG. 10). No homology with any previously reported bacteriocin sequences was found.

Summary of Results

Twenty-five isolates of Butyrivibrio were found to produce inhibitory activity detrimental to the growth of additional Butyrivibrio isolates using a deferred plating assay. The inhibitory activity was not the result of bacteriophage. Eighteen of these inhibitors were tested for protease sensitivity; all were sensitive towards digestion by proteases. Differences in both the host range (FIGS. 4A, 4B, 5A, 5B) and protease sensitivity profiles (FIG. 6) were found, suggesting that the same inhibitor is not produced by all of the strains. All inhibitors for which the molecular weight was determined had a molecular weight of less than 5 kDa. As the initial screening for inhibitory activity was limited to isolates of Butyrivibrio, it is unlikely that growth inhibition is a result of an end-product of metabolism, as the isolates are all closely related. All of these factors are consistent with the inhibitory activity displayed by these Butyrivibrio isolates being bacteriocins.

None of the inhibitors were produced at significant levels during growth in liquid L-10 medium. However increasing the amount of glucose from 0.2 to 2% (w/v) resulted in production of detectable levels of inhibitory activity in two representative strains, *B. fibrisolvens* AR10 and OR79.

A peptide was isolated from spent culture fluid from *B. fibrisolvens* AR10. The peptide was inhibitory to the growth of an indicator strain of *B. fibrisolvens*, had an identical protease sensitivity as the inhibitor produced in the deferred plating assay, and on this basis is now confirmed to be a bacteriocin. A partial sequence of the bacteriocin indicated no homology with any previously reported bacteriocin, therefore this peptide represents a new bacteriocin known as Butyrivibriocin AR10. Isolation and characterisation of a bacteriocin from *B. fibrisolvens* AR10, indicates that the inhibitory bacteriocin-like activities found throughout additional isolates of Butyrivibrio represent additional, new bacteriocins. These bacteriocins are inhibitory towards the growth of additional Butyrivibrio, non-Butyrivibrio rumen isolates, Listeria, and Clostridial isolates (FIGS. 5A and 5B).

Applicants have identified and described the characteristics of novel proteinaceous antibiotics derived from ruminal bacteria. Applicants have also identified and described the characteristics of ruminal bacteria which are producers of such proteinaceous antibiotics, as well as the means of selecting ruminal bacteria producers of proteinaceous antibiotics known as bacteriocins.

References

Arihara, K., Cassens, R. G., and Luchansky, J. B. 1993. Characterisation of bacteriocins from Enterococcus faecium with activity against *Listeria monocytogenes*. Internat. J. Food Microbiol. 19:123–134.

Barefoot, S. F., and Nettles, C. G. 1993. Antibiosis revisited: bacteriocins produced by dairy starter cultures. J.Dairy Sci. 76:2366–2379.

Bruno, M. E. C., and Montville, T. J. 1993. Common mechanistic action of bacteriocins from lactic acid bacteria. Appl. Envir. Microbiol. 59:3003–3010.

Bryant, M. P. 1986. Genus IV. Butyrivibrio. in Bergey's Manual of Systematic Bacteriology, Vol. 2. P. H. A. Sneath, N. S. Nair, M. E. Sharpe, and J. G. Holt (eds). Williams and Wilkins, Baltimore, Md., USA. pp 1376–1379.

Caldwell, D. R., and Bryant, M. P. 1966. Medium without rumen fluid for non-selective enumeration and isolation of rumen bacteria. Appl. Microbiol. 14:794–801.

Forster, R. J., Gong, J., and Teather, R. M. 1995. Phylogenetic relationships amongst Butyrivibrio-like isolates of rumen bacteria and the design of probes for determinative and community structure studies in the rumen. Abstracts of the Conference on Rumen Function, Chicago, Ill. Abstract Number 81, p. 47.

Iverson, W. G., and Mills, N. F. 1976. Bacteriocins of *Streptococcus bovis*. Can. J. Microbiol. 22:1040–1046.

Jack, R. W., Tagg, J. R., and Ray, B. 1995. Bacteriocins of Gram-Positive Bacteria. Microbiol. Rev. 59:171–200.

Klaenhammer, T. R. 1993. Genetics of bacteriocins produced by lactic acid bacteria. FEMS Microbiol. Rev. 12:39–86.

Nisen-Meyer, J., Havarstein, L. S., Holo, H., Sletten, K., and Nes., I. F. 1993. Association of the lactococcin A immunity factor with the cell membrane: purification and characterisation of the immunity factor. J. Gen. Microbiol. 139:1503–1509.

Odenyo, A. A., Mackie, R. I., Stahl, D. A., and White, B. A. 1993. The use of 16s rRNA-targeted oligonucleotide probes to study competition between ruminal fibrolytic bacteria: development of probes for Ruminococcus species and evidence for bacteriocin production. Appl. Env. Microbiol. 60:3688–3696.

Piard, J. C., and Desmazeaud, M. 1992. Inhibiting factors produced by lactic acid bacteria. Bacteriocins and other antibacterial substances. Lait 72:113–142.

Tagg, J. R., Dajani, A. S., and Wannamaker, L. W. 1976. Bacteriocins of Gram-positive bacteria. Bacteriol. Rev. 40:722–756.

What is claimed is:

1. A purified and isolated proteinaceous antibiotic which is a bacteriocin which, in nature, is produced by a ruminal bacterium selected from *Butyrivibrio fibrisolvens*.

2. A purified and isolated proteinaceous antibiotic, which is resistant to at least one gastric protease, exhibits a high level of hydrophobicity, is effective to inhibit growth of target organisms under anaerobic conditions and is ineffective to inhibit growth of target organisms in aerobic conditions, has a molecular weight of less than about 5 kDa, and which, in nature, is produced by a ruminal bacterium having a partial 16s rRNA gene sequence comprising the sequence depicted in any one of SEQ ID NO:1–SEQ ID NO:43.

3. A purified and isolated proteinaceous antibiotic according to claim 2, and which, in nature, is produced by an anaerobic Gram Positive microorganism having a vibrioid cellular shape, exhibiting resistance to Nalidixic acid, and producing butyric acid as a major metabolic end-product.

4. The purified and isolated proteinaceous antibiotic according to claim 2, having a total amino acid content as described in FIG. 9.

5. A process for identifing bacteriocin-producing bacteria comprising:
(a) selecting strains of niminal bacteria that are anaerobic, gram-positive, have a vibrioid cellular shape, exhibit resistance to Nalidixic acid and produce butyric acid as a major end product of fermentation; and
(b) screening said strains for the production of a compound having bacteriocin-like activity.

6. The process according to claim 5, wherein said strains of ruminal bacteria are strains having a partial 16s rRNA gene sequence comprising the sequence depicted in any one of SEQ ID NO:1–SEQ ID NO:43, or are strains shown to be related thereto through 16s rRNA analysis at a genus or species level.

7. The process according to claim 5, wherein said strains of ruminal bacteria are strains having a partial 16s rRNA gene sequence comprising the sequence depicted in any one of SEQ ID NO:1–SEQ ID NO:43.

8. The process according to claim 5, wherein said strains of ruminal bacteria are selected from *Butyrivibrio fibrisolvens*.

* * * * *

UNITED STATES PATENT AND TRADEMARK OFFICE
CERTIFICATE OF CORRECTION

PATENT NO.    : 6,255,080 B1
DATED         : July 3, 2001
INVENTOR(S)   : Ronald M. Teather et al.

It is certified that error appears in the above-identified patent and that said Letters Patent is hereby corrected as shown below:

Title page,
Item [56], OTHER PUBLICATIONS,
"Sneath et al.", delete – duplicate entry
"Hespell", delete fourth mention – duplicate entry
"Hespell", delete fifth mention – duplicate entry
"Ha", delete second mention – duplicate entry
"Jarvis", delete "Microbiol," and insert -- Microbiol. --;
"Tagg et al.", delete "*Reviews*(1976)" and insert -- Reviews (1976) --;
"Lindgren et al.", delete "agric." and insert -- Agric. --;
"Bryant", delete "*Systemic*" and insert -- *Systematic* --; delete "al" and insert -- al. --;
"Seale", delete "pp.9S-26S" and insert -- pp. 9S-26S --;
"Lindren et al.", delete "Lindren" and insert -- Lindgren --; delete "87(1990) pp. 149-163." and insert -- (1990) 87:149-163. --;
"Meghrous et al.", delete "Bifidobacterium" and insert -- *Bifidobacterium* --;
"Toba et al.", delete "*Microbiol,*" and insert -- *Microbiol.* --;
"Fitzsimmons et al.", delete "*Microbiol,*" and insert -- *Microbiol.* --; and
"Arihara et al.", delete "*Microbiol,*" and insert -- *Microbiol.* --.
"Forster et al.", delete "studes" and insert -- studies --;
"Hefford et al." delete "Butyrivibrio" and insert -- *Butyrivibrio* --; and
"Kobayashi et al.", delete "butyrivibrio" at both instances and insert -- *butyrivibrio* --.

Column 1,
Line 15, "delete "Butyrivibrio" and insert -- *Butyrivibrio* --.

Column 2,
Line 38, delete "Lactobacilli" and insert -- Lactobacilli --; and delete "Lactococci" and insert -- Lactococci --;
Line 39, delete "Pediococci" and insert -- Pediococci --; delete "Leuconostoc" and insert -- Leuconostoc --; and delete "Streptococci" and insert -- Streptococci --;
Line 54, delete "Propionibacter" and insert -- Propionibacter --;

Column 3,
Line 5, delete "Lysteria" and insert -- *Listeria* --;
Line 48, delete "lactis" and insert -- *lactis* --;

Column 4,
Line 17, delete "bacterlocins" and insert -- bacteriocins --;
Line 41, delete "Butyrivibrio" and insert -- *Butyrivibrio* --;
Line 43, delete "XIV" and insert -- *XIV* --;

UNITED STATES PATENT AND TRADEMARK OFFICE
CERTIFICATE OF CORRECTION

PATENT NO.    : 6,255,080 B1
DATED         : July 3, 2001
INVENTOR(S)   : Ronald M. Teather et al.

It is certified that error appears in the above-identified patent and that said Letters Patent is hereby corrected as shown below:

<u>Column 5,</u>
Lines 8, 24, 39, 45, 47 and 61, delete "Butyrivibrio" and insert -- *Butyrivibrio* --;
Line 31, delete "Listeria" and insert -- *Listeria* --; and delete "Clost Heidium" and insert -- *Clostridium* --;
Line 51, delete "Butyrivibrio" at both instances and insert -- *Butyrivibrio* --;
Line 56, delete "non-Butyrivibrio" and insert -- non-*Butyrivibrio* --; and delete "Butyrivibrio" and insert -- *Butyrivibrio* --;

<u>Column 6,</u>
Lines 15, 20, 37 and 54, delete "Butyrivibrio" and insert -- *Butyrivibrio* --;
Line 16, delete "non-Butyrivibrio" and replace with -- non-*Butyrivibrio* --;
Line 27, delete "-20° C." and insert -- 20°C --;
Lines 31, 42, 52 and 63, delete "37° C." and insert -- 37°C --;
Line 33, delete "non-Dutyrivibrio" and insert -- non-*Butyrivibrio* --;

<u>Column 7,</u>
Line 9, delete "anerobic" and insert -- anaerobic --;
Lines 13, 28, 55, 56 and 58, delete "Butyrivibrio" and insert -- *Butyrivibrio* --;
Lines 36, 40, 48, and 67, delete "37° C." and insert -- 37°C --;
Line 53, delete "non-Butyrivibrio" and insert -- non-*Butyrivibrio* --;
Line 53, delete "Listeria" and insert -- *Listeria* --;
Line 54, delete "Clostridium" and insert -- *Clostridium* --;

<u>Column 8,</u>
Line 1, delete "Butyrivibrio Fibrisolvens" and insert -- *Butyrivibrio fibrisolvens* --;
Line 5, delete "37° C." and insert -- 37°C --;
Line 12, delete "60 g/100ml,." and insert -- 60 g/100ml, --;
Lines 22, 40 and 55, delete "4° C." and insert -- 4°C --;
Line 26, delete "1oo" and insert -- 100 --;
Line 44, delete "0.19" and insert -- 0.1% --;
Line 49, delete "Ifractions" and insert -- fractions --;
Lines 57 and 66, delete "Butyrivibrio" and insert -- *Butyrivibrio* --;
Line 58, delete "Butyrivibrio fibrisolvens" and insert -- *Butyrivibrio fibrisolvens* --;
Line 59, delete "Butyrivibrio crossotus" and insert -- *Butyrivibrio crossouts* --;
Line 62, delete "4B ." and insert -- 4B. -- period;

UNITED STATES PATENT AND TRADEMARK OFFICE
CERTIFICATE OF CORRECTION

PATENT NO.   : 6,255,080 B1
DATED        : July 3, 2001
INVENTOR(S)  : Ronald M. Teather et al.

It is certified that error appears in the above-identified patent and that said Letters Patent is hereby corrected as shown below:

Column 10,
Line 18, delete "eFlect" and insert -- effect --;
Line 39, delete "a-chymotrypsin" and insert -- α-chymotrypsin --;
Lines 58 and 60, delete "Butyrivibrio" and insert -- *Butyrivibrio* --;

Column 11,
Lines 3, 6 and 24, delete "Butyrivibrio" and insert -- *Butyrivibrio* --;
Line 26, delete "Butyrivibrio" and insert -- *Butyrivibrio* --; and delete "non-Butyrivbrio" and insert -- non-*Butyrivibrio* --;
Line 27, delete "Listeria" and insert -- *Listeria* --; and delete "Clostridial" and insert -- *Clostridial* --;
Line 38, delete "Enterococcus" and insert -- *Enterococcus* --;
Line 39, delete "faecium" and insert -- *faecium* --;
Line 42, delete ""J.Dairy" and insert -- J. Dairy --;

Column 12,
Line 7, delete "pp" and insert -- pp. --; and
Line 35, delete "Ruminococcus" and insert -- *Ruminococcus* --.

Column 45,
Line 15, delete "identifing" and insert -- identifying --; and
Line 17, delete "niminal" and insert -- ruminal --.

Signed and Sealed this

Twenty-sixth Day of August, 2003

JAMES E. ROGAN
*Director of the United States Patent and Trademark Office*

SEQUENCE LISTING (1) GENERAL INFORMATION:

(iii) NUMBER OF SEQUENCES:  44

(2) INFORMATION FOR SEQ ID NO: 1:

(i) SEQUENCE CHARACTERISTICS:
      (A) LENGTH: 196 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: butyrivibrio fibrisolvens
      (B) STRAIN: ob244

(xi) SEQUENCE DESCRIPTION: SEQ ID NO: 1:

```
CATGCAAGTC GAACGGAGAT TAGACGCTGA CGAGACTTCG GTCAAATCTT GTTTAATCTT      60

AGTGGCGGAC GGGTGAGTAA CGCGTGGGCA ACCTGCCTCA TACTGGGGGA TAACAGTTGG     120

AAACGACTGT TAATACCGCA TAAGNGCACA GAGTCGCATG ACTCAGTGTG AAAAACTCCG     180

GTGGTATGAG ATGGGC                                                     196
```

(2) INFORMATION FOR SEQ ID NO: 2:

(i) SEQUENCE CHARACTERISTICS:
        (A) LENGTH: 198 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibio fibrisolvens
        (B) STRAIN: ob250

(xi) SEQUENCE DESCRIPTION: SEQ ID NO: 2:

```
CACATGCAAG TCGAACGGAT TTTGCTCGCT GCAGAGACTT CGGTCGAAGC TTGAGTAAAG      60

TTAGTGGCGG ACGGGTGAGT AACGCGTGGG CAACCTGCCT CATACTGGGG GATAACAGTT     120

GGAAACGACT GTTAATACCG CATAAGCGNA CAGAGTCGCA TGACTCAGTG TGAAAAACTC     180

CGGTGGTATG AGATGGGC                                                   198
```

(2) INFORMATION FOR SEQ ID NO: 3:

(i) SEQUENCE CHARACTERISTICS:
        (A) LENGTH: 196 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: actf2

(xi) SEQUENCE DESCRIPTION: SEQ ID NO: 3:

```
CACATGCAAG TCGAACGGAG TTATTCGCTG ATGAAGCTTC GGCAGATTCT TGAATAACTT      60

AGTGGCGGAC GGGTGAGTAA CGCGTGGGTA ACCTGCCTCA TACAGGGGGA TAGCAGTTGG     120

AAACGACTGA TAACACCGCA TAAGCGCACA GTATCGCATG ATACAGTGTG AAAATATTTA     180

TAGGTATGAG ATGGAC                                                     196
```

(2) INFORMATION FOR SEQ ID NO: 4:

(i) SEQUENCE CHARACTERISTICS:
        (A) LENGTH: 198 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: butyrivibrio fibrisolvens
    (B) STRAIN: ar10-or433

(xi) SEQUENCE DESCRIPTION: SEQ ID NO: 4:

```
CACATGCAAG TCGAACGGAG AATTTACGCT GATGAAGCTT CGGCAGATTC TTGTAAATTC    60

TTAGTGGCGG ACGGGTGAGT AACGCGTGGG CAACCTGCCT CATACTGGGG GATAACAGCT   120

GGAAACGACT GTTAATACCG CATAAGCGCA CGGTATCGCA TGATACAGTG TGAAAAACTC   180

CGGTGGTATG AGATGGGC                                                 198
```

(2) INFORMATION FOR SEQ ID NO: 5:

(i) SEQUENCE CHARACTERISTICS:
        (A) LENGTH: 195 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrvibrio fibrisolvens
        (B) STRAIN: atcc-19171

(xi) SEQUENCE DESCRIPTION: SEQ ID NO: 5:

```
ACATGCAAGT CGAACGGAGT TATTCGCTGA TGAAGCTTCG GCAGAATCTT GAATAACTTA    60

GTGGCGGACG GGTGAGTAAC GCGTGGGTAA CCTGCCTCAT ACAGGGGAT AGCAGTTGGA   120

AACGACTGAT AACACCGCAT AAGCGCACAG TGTCGCATGA CACAGTGTGA AAATATTTAT   180

AGGTATGAGA TGGAC                                                    195
```

(2) INFORMATION FOR SEQ ID NO: 6:

(i) SEQUENCE CHARACTERISTICS:
        (A) LENGTH: 188 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrvibrio fibrisolvens
        (B) STRAIN: atcc 28175

(xi) SEQUENCE DESCRIPTION: SEQ ID NO: 6:

```
CACATGCAAG TCGAACGAAG CACTTCATAA AGCTTGCTTT AAGAAGTGAC TTAGTGGCGG    60

ACGGGTGAGT AACGCGTGGG TAACCTGCCT TACACAGGGG GATAACAGTT AGAAATGACT   120

GCTAATACCG CATAAAACAG CAGAGTCGCA TGACTCAACT GTCAAAGATT TATCGGTGTA   180

AGATGGAC                                                            188
```

(2) INFORMATION FOR SEQ ID NO: 7:

(i) SEQUENCE CHARACTERISTICS:
        (A) LENGTH: 199 base pairs (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: butyrivibrio fibrisolvens
            (B) STRAIN: ob248

(xi) SEQUENCE DESCRIPTION: SEQ ID NO: 7:

CACATGCAAG TCGAACGGAG ATATAACGCT GCATGAGACT TCGGTCAAAG CTTGTTGTAT     60

CTTAGTGGCG GACGGGTGAG TAACGCGTGG GCAACCTGCC TCATACTGGG GGATAACAGT    120

TGGAAACGGC TGTTAATACC GCATAAGCGC ACAGAGTCGC ATGACTCAGT GTGAAAAACT    180

CCGGTGGTAT GAGATGGGC                                                 199

(2) INFORMATION FOR SEQ ID NO: 8:

(i) SEQUENCE CHARACTERISTICS:
            (A) LENGTH: 198 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: butyrivibrio fibrisolvens
            (B) STRAIN: ob251

(xi) SEQUENCE DESCRIPTION: SEQ ID NO: 8:

CACATGCAAG TCGAACGGAG TTTACTCGCT GATGAAGCTT CGGCAGAATC TTGAGTAAAC     60

TTAGTGGCGG ACGGGTGAGT AACGCGTGGG CAACCTGCCT CATACTGGGG GATAGCAGTT    120

GGAAACGACT GATAATACCG CATAAGCGNA CGGTATCGCA TGATACAGTG TGAAAAACTC    180

CGGTGGTATG AGATGGGC                                                  198

(2) INFORMATION FOR SEQ ID NO: 9:

(i) SEQUENCE CHARACTERISTICS:
            (A) LENGTH: 198 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: butyrivibrio fibrisolvens
            (B) STRAIN: x10c34

(xi) SEQUENCE DESCRIPTION: SEQ ID NO: 9:

CACATGCAAG TCGAACGGAG ATTAGACGCT GACGAGACTT CGGTCAAATC TTGTTTAATC     60

TTAGTGGCGG ACGGGTGAGT AACGCGTGGG CAACCTGCCT CATACTGGGG GATAACAGTT    120

GGAAACGACT GTTAATACCG CATAAGCGCA CAGAGTCGCA TGACTCAGTG TGAAAAACTC    180

CGGTGGTATG AGATGGGC                                                  198

(2) INFORMATION FOR SEQ ID NO: 10:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: h10b (xi) SEQUENCE DESCRIPTION: SEQ ID NO: 10:

CACATGCAAG TCGAACGAAG CAATTTCTTA CGATCCCTTC GGGGTGACGA GTTATTGACT      60

GAGTGGCGGA CGGGTGAGTA ACGCGTGGGT AACCTGCCTT GTACAGGGGG ACAACAGTTG     120

GAAACGACTG CTAATACCGC ATAAGCGCAC AGTATCGCAT GGTACAGTGT GAAAAGTTTT     180

TTCGGTACAA GATGGAC                                                  197

(2) INFORMATION FOR SEQ ID NO: 11:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: or2-h10b (xi) SEQUENCE DESCRIPTION: SEQ ID NO: 11:

CACATGCAAG TCGAACGAAG CAACTTATTA CGATCCCTTC GGGGTGACGA GTTATTGACT      60

GAGTGGCGGA CGGGTGAGTA ACGCGTGGGT AACCTGCCTT GTACAGGGGG ACAACAGTTG     120

GAAACGACTG CTAATACCGC ATAAGCGCAC AGTATCGCAT GGTACAGTGT GAAAAGTTTT     180

TTCGGTACAA GATGGAC                                                  197

(2) INFORMATION FOR SEQ ID NO: 12:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: or85

(xi) SEQUENCE DESCRIPTION: SEQ ID NO: 12:

```
CACATGCAAG TCGAACGAAG CAATTTTCTA CGATCCTTTC GGGGTGACGG ATTATTGACT      60

GAGTGGCGGA CGGGTGAGTA ACGCGTGGGT AACCTACCTT GTACAGGGGG ACAACAGTTG     120

GAAACGACTG CTAATACCGC ATAAGCGCAC AGCATCGCAT GATGCAGTNT GAAAAGTTTT     180

TTCGGTACAA GATGGAC                                                    197
```

(2) INFORMATION FOR SEQ ID NO: 13:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: ar73-or435

(xi) SEQUENCE DESCRIPTION: SEQ ID NO: 13:

```
CACATGCAAG TCGAACGAAG CAATTTTCTA CGATCCCTTC GGGGTGACGG ATTATTGACT      60

GAGTGGCGGA CGGGTGAGTA ACGCGTGGGT AACCTACCTT GTACAGGGGG ACAACAGTTG     120

GAAACGACTG CTAATACCGC ATAAGCGCAC AGCATCGCAT GATGCAGTGT GAAAAGTTTT     180

TTCGGTACAA GATGGAC                                                    197
```

(2) INFORMATION FOR SEQ ID NO: 14:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: cf3

(xi) SEQUENCE DESCRIPTION: SEQ ID NO: 14:

```
CACATGCAAG TCGAACGAAG CAATTTCTTA CGATCCCTTC GGGGTGACGA GATATTGACT      60

GAGTGGCGGA CGGGTGAGTA ACGCGTGGGT AACCTGCCTT GTACAGGGGG ACAACAGTTG     120

GAAACGACTG CTAATACCGC ATAAGCGCAC AGCATCGCAT GATGCAGTGT GAAAAGTTTT     180

TTCGGTACAA GATGGAC                                                    197
```

(2) INFORMATION FOR SEQ ID NO: 15:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: GSIII (xi) SEQUENCE DESCRIPTION: SEQ ID NO: 15:

```
CACATGCAAG TCGAACGAAG CAATTTTCCA CGATCCCTTC GGGGTGACGG ATTATTGACT      60

GAGTGGCGGA CGGGTGAGTA ACGCGTGGGT AACCTACCTT GTACAGGGGG ACAACAGTTG     120

GAAACGACTG CTAATACCGC ATAAGCGCAC AGCATCGCAT GATGCAGTGT GAAAAGTTTT     180

TTCGGTACAA GATGGAC                                                   197
```

(2) INFORMATION FOR SEQ ID NO: 16:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: nor37

(xi) SEQUENCE DESCRIPTION: SEQ ID NO: 16:

```
CACATGCAAG TCGAACGAAG CAATTTTCTA CGATCCCTTC GGGGTGACGG ATTATTGACT      60

GAGTGGCGGA CGGGTGAGTA ACGCGTGGGT AACCTACCTT GTACAGGGGG ACAACAGTTG     120

GAAACGACTG CTAATACCGC ATAAGCGCAC AGCATCGCAT GATGCAGTGT GAAAAGTTTT     180

TTCGGTACAA GATGGAC                                                   197
```

(2) INFORMATION FOR SEQ ID NO: 17:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: ob236

(xi) SEQUENCE DESCRIPTION: SEQ ID NO: 17:

```
CACATGCAAG TCGAACGAAG CAATTTTCTA CGATCCCTTC GGGGTGACGG ATTATTGACT      60

GAGTGGCGGA CGGGTGAGTA ACGCGTGGGT AACCTACCTT GTACAGGGGG ACAACAGTTG     120

GAAACGACTG CTAATACCGC ATAAGCGCAC AGCATCGCAT GATGCAGTGT GAAAAGTTTT     180

TTCGGTACAA GATGGAC                                                   197
```

(2) INFORMATION FOR SEQ ID NO: 18:

```
        (i) SEQUENCE CHARACTERISTICS:
            (A) LENGTH: 197 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: butyrivibrio fibrisolvens
            (B) STRAIN: or76

(xi) SEQUENCE DESCRIPTION: SEQ ID NO: 18:

CACATGCAAG TCGAACGAAG CAATTTTCTA CGATCCCTTC GGGGTGACGG ATTATTGACT      60

GAGTGGCGGA CGGGTGAGTA ACGCGTGGGT AACCTACCTT GTACAGGGGG ACAACAGTTG     120

GAAACGACTG CTAATACCGC ATAAGCGNAC AGCATCGCAT GATGCAGTNT GAAAAGTTTT     180

TTCGGTACAA GATGGAC                                                   197

(2) INFORMATION FOR SEQ ID NO: 19:

(i) SEQUENCE CHARACTERISTICS:
            (A) LENGTH: 197 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: butyrivibrio fibrisolvens
            (B) STRAIN: or77

(xi) SEQUENCE DESCRIPTION: SEQ ID NO: 19:

CACATGCAAG TCGAACGAAG CAATTTTCTA CGATCCTTTC GGGGTGACGG ATTATTGACT      60

GAGTGGCGGA CGGGTGAGTA ACGCGTGGGT AACCTACCTT GTACAGGGGG ACAACAGTTG     120

GAAACGACTG CTAATACCGC ATAAGCGCAC AGCATCGCAT GATGCAGTGT GAAAAGTTTT     180

TTCGGTACAA GATGGAC                                                   197

(2) INFORMATION FOR SEQ ID NO: 20:

(i) SEQUENCE CHARACTERISTICS:
            (A) LENGTH: 197 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: butyrivibrio fibrisolvens
            (B) STRAIN: or78

(xi) SEQUENCE DESCRIPTION: SEQ ID NO: 20:

CACATGCAAG TCGAACGAAG CAATTTTCTA CGATCCTTTC GGGGTGACGG ATTATTGACT      60
```

```
GAGTGGCGGA CGGGTGAGTA ACGCGTGGGT AACCTACCTT GTACAGGGGG ACAACAGTTG      120

GAAACGACTG CTAATACCGC ATAAGCGCAC AGCATCGCAT GATGCAGTNT GAAAAGTTTT      180

TTCGGTACAA GATGGAC                                                     197
```

(2) INFORMATION FOR SEQ ID NO: 21:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: or79

(xi) SEQUENCE DESCRIPTION: SEQ ID NO: 21:

```
CACATGCAAG TCGAACGAAG CAATTTTCTA CGATCCCTTC GGGGTGACAG ATTATTGACT       60

GAGTGGCGGA CGGGTGAGTA ACGCGTGGGT AACCTACCTT GTACAGGGGG ACAACAGTTG      120

GAAACGACTG CTAATACCGC ATAAGCGNAC AGCATCGCAT GATGCAGTGT GAAAAGTTTT      180

TTCGGTACAA GATGGAC                                                     197
```

(2) INFORMATION FOR SEQ ID NO: 22:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: or84

(xi) SEQUENCE DESCRIPTION: SEQ ID NO: 22:

```
CACATGCAAG TCGAACGAAG CAATTTTCTA CGATCCTTTC GGGGTGACGG ATTATTGACT       60

GAGTGGCGGA CGGGTGAGTA ACGCGTGGGT AACCTACCTT GTACAGGGGG ACAACAGTTG      120

GAAACGACTG CTAATACCGC ATAAGCGCAC AGCATCGCAT GATGCAGTNT GAAAAGTTTT      180

TTCGGTACAA GATGGAC                                                     197
```

(2) INFORMATION FOR SEQ ID NO: 23:

(i) SEQUENCE CHARACTERISTICS:
        (A) LENGTH: 195 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: butyrivibrio fibrisolvens
            (B) STRAIN: e14 or392

(xi) SEQUENCE DESCRIPTION: SEQ ID NO: 23:

CATGCAAGTC GAACGAAGCA ATTTTCTACG ATCCTTTCGG GGTGACGGAT TATTGACTGA    60

GTGGCGGACG GGTGAGTAAC GCGTGGGTAA CCTACCTTGT ACAGGGGAC AACAGTTGGA    120

AACGACTGCT AATACCGCAT AAGCGCACAG CATCGCATGA TGCAGTGTGA AAAGTTTTTT    180

CGGTACAAGA TGGAC    195

(2) INFORMATION FOR SEQ ID NO: 24:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: ar27-or434

(xi) SEQUENCE DESCRIPTION: SEQ ID NO: 24:

CACATGCAAG TCGAACGAAG CAATTTATCA CGATCCTTTC GGGGTGACGA TTTATTGACT    60

TAGTGGCGGA CGGGTGAGTA ACGCGTGGGT AACCTACCTT GTACAGGGGG ACAACAGTTG    120

GAAACGACTG CTAATACCGC ATAAGCGCAC GGTATCGCAT GATACAGTGT GAAAAGTTTT    180

TTCGGTACAA GATGGAC    197

(2) INFORMATION FOR SEQ ID NO: 25:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: 49-or107

(xi) SEQUENCE DESCRIPTION: SEQ ID NO: 25:

CACATGCAAG TCGAACGAAG CAGTTTATCA CGATCCCTTC GGGGTGACGA TTTACTGACT    60

GAGTGGCGGA CGGGTGAGTA ACGCGTGGGT AACCTGCCTT GTACAGGGGG ACAACAGTTG    120

GAAACGACTG CTAATACCGC ATAAGCGCAC GGAATCGCAT GATTTTGTGT GAAAAGATTT    180

ATCGGTACAA GATGGAC    197

(2) INFORMATION FOR SEQ ID NO: 26:

(i) SEQUENCE CHARACTERISTICS:
        (A) LENGTH: 196 base pairs
        (B) TYPE: nucleic acid
        (C) STRANDEDNESS: double (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: butyrivibrio fibrisolvens
    (B) STRAIN: ob232

(xi) SEQUENCE DESCRIPTION: SEQ ID NO: 26:

```
ACATGCAAGT CGAACGAAGC AACTTATTAC GATCCCTTCG GGGTGACGAT TTGTTGACTG      60

AGTGGCGGAC GGGTGAGTAA CGCGTGGGTA ACCTACCTTG TACAGGGGGA CAACAGTTGG     120

AAACGACTGC TAATACCGCA TAAGCGCACA GCTTCGCATG AAGCAGTGTG AAAAGTTATT    180

TCGGTACAAG ATGGAC                                                     196
```

(2) INFORMATION FOR SEQ ID NO: 27:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: or36

(xi) SEQUENCE DESCRIPTION: SEQ ID NO: 27:

```
CACATGCAAG TCGAACGAAG CAACTTATTA CGATCCCTTC GGGGTGACGA TTTGTTGACT      60

GAGTGGCGGA CGGGTGAGTA ACGCGTGGGT AACCTGCCTT GTACAGGGGG ACAACAGTTG    120

GAAACGACTG CTAATACCGC ATAAGCGCAC AGCTTCGCAT GAAGTAGTGT GAAAAGATTT    180

TTCGGTACAA GATGGAC                                                    197
```

(2) INFORMATION FOR SEQ ID NO: 28:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: or37

(xi) SEQUENCE DESCRIPTION: SEQ ID NO: 28:

```
CACATGCAAG TCGAACGAAG CAACTTATTA CGATCCCTTC GGGGTGACGA TTTGTTGACT      60

GAGTGGCGGA CGGGTGAGTA ACGCGTGGGT AACCTGCCTT GTACAGGGGG ACAACAGTTG    120

GAAACGACTG CTAATACCGC ATAAGCGCAC AGCTTCGCAT GAAGTAGTGT GAAAAGATTT    180

TTCGGTACAA GATGGAC                                                    197
```

(2) INFORMATION FOR SEQ ID NO: 29:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: or38

(xi) SEQUENCE DESCRIPTION: SEQ ID NO: 29:

```
CACATGCAAG TCGAACGAAG CAACTTATTA CGATCCCTTC GGGGTGACGA TTTGTTGACT      60

GAGTGGCGGA CGGGTGAGTA ACGCGTGGGT AACCTGCCTT GTACAGGGGG ACAACAGTTG     120

GAAACGACTG CTAATACCGC ATAAGCGCAC AGCTTCGCAT GAAGTAGTGT GAAAAGATTT     180

TTCGGTACAA GATGGAC                                                    197
```

(2) INFORMATION FOR SEQ ID NO: 30:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: pi-7-or106

(xi) SEQUENCE DESCRIPTION: SEQ ID NO: 30:

```
CACATGCAAG TCGAACNAAG CAACTTATTA CGATCCCTTC GGGGTGACGA TTTGTTGACT      60

GAGTGGCGGA CGGGTGAGTA ACGCGTGGGT AACCTGCCTT GTACAGGGGG ACAACAGTTG     120

GAAACGACTG CTAATACCGC ATAAGCGNAC AGCTTCGCAT GAAGCAGTGT GAAAAGTTAT     180

TTCGGTACAA GATGGAC                                                    197
```

(2) INFORMATION FOR SEQ ID NO: 31:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: or35

(xi) SEQUENCE DESCRIPTION: SEQ ID NO: 31:

```
CACATGCAAG TCGAACGAAG CAACTTATTA CGATCCCTTC GGGGTGACGA TTTGTTGACT      60

GAGTGGCGGA CGGGTGAGTA ACGCGTGGGT AACCTGCCTT GTACAGGGGG ACAACAGTTG     120

GAAACGACTG CTAATACCGC ATAAGCGCAC AGCTTCGCAT GAAGTAGTGT GAAAAGATTT     180

TTCGGTACAA GATGGAC                                                   197

(2) INFORMATION FOR SEQ ID NO: 32:

(i) SEQUENCE CHARACTERISTICS:
          (A) LENGTH: 197 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: butyrvibrio fibrisolvens
          (B) STRAIN: uc12254

(xi) SEQUENCE DESCRIPTION: SEQ ID NO: 32:

CACATGCAAG TCGAACGAAG CAGTTTATCA CGATCCCTTC GGGGTGACGA TTTACTGACT      60

GAGTGGCGGA CGGGTGAGTA ACGCGTGGGT AACCTGCCTT GTACAGGGGG ACAACAGTTG     120

GAAACGACTG CTAATACCGC ATAAGCGCAC GGAATCGCAT GATTTGTGT GAAAAGATTT     180

ATCGGTACAA GATGGAC                                                   197

(2) INFORMATION FOR SEQ ID NO: 33:

(i) SEQUENCE CHARACTERISTICS:
          (A) LENGTH: 197 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: butyrivibrio fibrisolvens
          (B) STRAIN: vv1

(xi) SEQUENCE DESCRIPTION: SEQ ID NO: 33:

CACATGCAAG TCGAACGAAG CAGTTTATCA CGATCCCTTC GGGGTGACGA TTTACTGACT      60

GAGTGGCGGA CGGGTGAGTA ACGCGTGGGT AACCTGCCTT GTACAGGGGG ACAACAGTTG     120

GAAACGACTG CTAATACCGC ATAAGCGCAC GGAATCGCAT GATTTGTGT GAAAAGATTT     180

ATCGGTACAA GATGGAC                                                   197

(2) INFORMATION FOR SEQ ID NO: 34:

(i) SEQUENCE CHARACTERISTICS:
          (A) LENGTH: 197 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO
```

(iv) ANTI-SENSE: NO (vi) ORIGINAL SOURCE:
              (A) ORGANISM: butyrivibrio fibrisolvens
              (B) STRAIN: ob143

(xi) SEQUENCE DESCRIPTION: SEQ ID NO: 34:

CACATGCAAG TCGAACGAAG CATTTACTTA CGATCCCTTC GGGGTGACGA GTTTATGACT        60

GAGTGGCGGA CGGGTGAGTA ACGCGTGGGT AACCTACCTT ATACAGGGGG ACAACAGTTG       120

GAAACGACTG CTAATACCGC ATAAGCGCAC GATGTTGCAT GACAACGTGT GAAAAGATTT       180

ATCGGTATAA GATGGAC                                                     197

(2) INFORMATION FOR SEQ ID NO: 35:

(i) SEQUENCE CHARACTERISTICS:
              (A) LENGTH: 197 base pairs
              (B) TYPE: nucleic acid
              (C) STRANDEDNESS: double
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: butyrivibrio fibrisolvens
              (B) STRAIN: ob148

(xi) SEQUENCE DESCRIPTION: SEQ ID NO: 35:

CACATGCAAG TCGAACGAAG CATTTACTTA CGATCCCTTC GGGGTGACGA GTTAATGACT        60

GAGTGGCGGA CGGGTGAGTA ACGCGTGGGT AACCTACCTT ATACAGGGGG ACAACAGTTG       120

GAAACGACTG CTAATACCGC ATAAGCGCAC GATGTTGCAT GACAACGTGT GAAAAGATTT       180

ATCGGTATAA GATGGAC                                                     197

(2) INFORMATION FOR SEQ ID NO: 36:

(i) SEQUENCE CHARACTERISTICS:
              (A) LENGTH: 197 base pairs
              (B) TYPE: nucleic acid
              (C) STRANDEDNESS: double
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: butyrivibrio fibrisolvens
              (B) STRAIN: ob149

(xi) SEQUENCE DESCRIPTION: SEQ ID NO: 36:

CACATGCAAG TCGAACGAAG CATTTACTTA CGATCCCTTC GGGGTGACGA GTTAATGACT        60

GAGTGGCGGA CGGGTGAGTA ACGCGTGGGT AACCTACCTT ATACAGGGGG ACAACAGTTG       120

GAAACGACTG CTAATACCGC ATAAGCGCAC GATGTTGCAT GACAACGTGT GAAAAGATTT       180

ATCGGTATAA GATGGAC                                                     197

(2) INFORMATION FOR SEQ ID NO: 37:

(i) SEQUENCE CHARACTERISTICS:

(A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: ob150

(xi) SEQUENCE DESCRIPTION: SEQ ID NO: 37:

CACATGCAAG TCGAACGAAG CATTTACTTA CGATCCCTTC GGGGTGACGA GTTAATGACT      60

GAGTGGCGGA CGGGTGAGTA ACGCGTGGGT AACCTACCTT ATACAGGGGG ACAACAGTTG     120

GAAACGACTG CTAATACCGC ATAAGCGCAC GATGTTGCAT GACAACGTGT GAAAAGATTT     180

ATCGGTATAA GATGGAC                                                    197

(2) INFORMATION FOR SEQ ID NO: 38:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: ob153

(xi) SEQUENCE DESCRIPTION: SEQ ID NO: 38:

CACATGCAAG TCGAACGAAG CATTTACTTA CGATCCCTTC GGGGTGACGA GTTTATGACT      60

GAGTGGCGGA CGGGTGAGTA ACGCGTGGGT AACCTACCTT ATACAGGGGG ACAACAGTTG     120

GAAACGACTG CTAATACCGC ATAAGCGCAC GATGTTGCAT GACAACGTGT GAAAAGATTT     180

ATCGGTATAA GATGGAC                                                    197

(2) INFORMATION FOR SEQ ID NO: 39:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: ob155

(xi) SEQUENCE DESCRIPTION: SEQ ID NO: 39:

CACATGCAAG TCGAACGAAG CATTTACTTA CGATCCCTTC GGGGTGACGA GTTTATGACT      60

GAGTGGCGGA CGGGTGAGTA ACGCGTGGGT AACCTACCTT ATACAGGGGG ACAACAGTTG     120

```
GAAACGACTG CTAATACCGC ATAAGCGCAC GATGTTGCAT GACAACGTGT GAAAAGATTT      180

ATCGGTATAA GATGGAC                                                    197
```

(2) INFORMATION FOR SEQ ID NO: 40:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: ob157

(xi) SEQUENCE DESCRIPTION: SEQ ID NO: 40:

```
CACATGCAAG TCGAACGAAG CATTTACTTA CGATCCCTTC GGGGTGACGA GTTTATGACT       60

GAGTGGCGGA CGGGTGAGTA ACGCGTGGGT AACCTACCTT ATACAGGGGG ACAACAGTTG      120

GAAACGACTG CTAATACCGC ATAAGCGCAC GATGTTGCAT GACAACGTGT GAAAAGATTT      180

ATCGGTATAA GATGGAC                                                    197
```

(2) INFORMATION FOR SEQ ID NO: 41:

(i) SEQUENCE CHARACTERISTICS:
        (A) LENGTH: 195 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: ob189

(xi) SEQUENCE DESCRIPTION: SEQ ID NO: 41:

```
CACATGCAAG TCGAACGAAG CATTTACTTA CGATCCCTTC GGGGTGACGA GTTTATGACT       60

GAGTGCGGAC GGGTGAGTAA CGCGTGGGTA ACCTACCTTA TACAGGGGGA ACAGTTGGA      120

AACGACTGCT AATACCGCAT AAGCGCACAG CTTTGCATGA AGCGGTGTGA AAGATTTAT      180

CGGTATAAGA TGGAC                                                      195
```

(2) INFORMATION FOR SEQ ID NO: 42:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens (B) STRAIN: ob156

(xi) SEQUENCE DESCRIPTION: SEQ ID NO: 42:

CACATGCAAG TCGAACGAAG CATTTACTTA CGATCCCTTC GGGGTGACGA GTTAATGACT    60

GAGTGGCGGA CGGGTGAGTA ACGCGTGGGT AACCTACCTT ATACAGGGGG ACAACAGTTG   120

GAAACGACTG CTAATACCGC ATAAGCGCAC GATGTTGCAT GACAACGTGT GAAAAGATTT   180

ATCGGTATAA GATGGAC                                                 197

(2) INFORMATION FOR SEQ ID NO: 43:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: butyrivibrio fibrisolvens
        (B) STRAIN: ob192

(xi) SEQUENCE DESCRIPTION: SEQ ID NO: 43:

CACATGCAAG TCGAACGAAG CATTTACTTA CGATCCCTTC GGGGTGACGA GTTTATGACT    60

GAGTGGCGGA CGGGTGAGTA ACGCGTGGGT AACCTACCTT ATACAGGGGG ACAACAGTTG   120

GAAACGACTG CTAATACCGC ATAAGCGCAC GATGTTGCAT GACAACGTGT GAAAAGATTT   180

ATCGGTATAA GATGGAC                                                 197

(2) INFORMATION FOR SEQ ID NO:44:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Peptide
        (B) LOCATION: 1..22
        (D) OTHER INFORMATION: /product= "Unknown amino acids at
            pos. 9, 16, 21, 22"

(xi) SEQUENCE DESCRIPTION: SEQ ID NO:44:

Met Gly Ile Gln Leu Ala Pro Ala Xaa Tyr Gln Asp Ile Val Asn Xaa
1               5                  10                  15

Val Ala Ala Gly Xaa Xaa
            20